United States Patent
Neyts et al.

(10) Patent No.: US 8,404,707 B2
(45) Date of Patent: Mar. 26, 2013

(54) IMIDAZO [1, 2-A] PYRROLO [3, 2-C] PYRIDINE COMPOUNDS USEFUL AS PESTIVIRUS INHIBITORS

(75) Inventors: Johan Neyts, Kessel-Lo (BE); Jan Paeshuyse, Kessel-Lo (BE); Olivier Chavignon, Clermont-Ferrand (FR); Jean-Michel Chezal, Clermont-Ferrand (FR); Vincent Gaumet, Clermont-Ferrand (FR); Alain Gueiffier, Tours (FR); Jean-Claude Teulade, Clermont-Ferrand (FR)

(73) Assignees: Universite d'Auvergne Clermont 1, Clermont-Ferrand (FR); Universite Francois Rabelais Tours, Tours Cedex 1 (FR); Kathlieke Universiteit Leuven, Leuven (BE)

( * ) Notice: Subject to any disclaimer, the term of this patent is extended or adjusted under 35 U.S.C. 154(b) by 564 days.

(21) Appl. No.: 12/518,993

(22) PCT Filed: Dec. 14, 2007

(86) PCT No.: PCT/BE2007/000127
§ 371 (c)(1),
(2), (4) Date: Dec. 30, 2009

(87) PCT Pub. No.: WO2008/070937
PCT Pub. Date: Jun. 19, 2008

(65) Prior Publication Data
US 2010/0093781 A1 Apr. 15, 2010

(30) Foreign Application Priority Data
Dec. 14, 2006 (GB) .................................. 0624983.3

(51) Int. Cl.
*A61K 31/437* (2006.01)
*C07D 471/14* (2006.01)
(52) U.S. Cl. .......................................... 514/293; 546/82
(58) Field of Classification Search .................. 514/293; 546/82
See application file for complete search history.

(56) References Cited

U.S. PATENT DOCUMENTS
6,020,342 A * 2/2000 Tanaka et al. ................. 514/292

OTHER PUBLICATIONS

Parish et al. J. Med. Chem. 1982, 25, 98-102.*
Paeshuyse et al. J. Virol. 2007, 81, 11046-11053.*
Jordan, V. C. Nature Reviews: Drug Discovery, 2, 2003, p. 205-213.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Chezal et al. J. Org. Chem. 2001, 66, 6576-6584.*
Chezal et al., "Heterocyclization of Functionalized Vinylic Derivatives of Imidazo [1,2-a] pyridines," *J. Org. Chem.* 66:6576-6584 (2001).
Paeshuyse et al., "The Imidazopyrrolopyridine Analogue AG110 is a Novel, Highly Selective Inhibitor of Pestivirus Replication and Targets the Viral RNA-Dependent RNA Polymerase," Oral Session V: Hepatitis Viruses II, Herpesviruses II and Poxviruses II, *Program and Abstracts/Antiviral Res.* 74:A39 (abstract 30) (2007).
Paeshuyse et al., "A Novel, Highly Selective Inhibitor of Pestivirus Replication That Targets the Viral RNA-Dependent RNA Polymerase," *J. Virol.* 80:149-160 (2006).
Sun et al., "Specific Inhibition of Bovine Viral Diarrhea Virus Replicase," *J. Virol.* 77:6753-6760 (2003).
International Search Report for International Application No. PCT/BE2007/000127, mailed Jul. 9, 2008.
Written Opinion for International Application No. PCT/BE2007/000127, mailed Jul. 9, 2008.

* cited by examiner

*Primary Examiner* — Joseph Kosack
*Assistant Examiner* — Matthew Coughlin
(74) *Attorney, Agent, or Firm* — Clark & Elbing LLP

(57) ABSTRACT

The present invention relates to a series of novel imidazo[1,2-α]pyrrolo[3,2-c]pyridines (or also named 6H-1,3a,6-Triaza-αy-indacenes) and derivatives thereof, according to formula: (I); The present invention also relates to processes for the preparation of imidazo[1,2-α]pyrrolo[3,2-c]pyridines, their use as. a, medicine, their use to treat or prevent viral infections and their use to manufacture a medicine to treat or prevent viral infections, particularly infections with viruses belonging to the family of the Flaviviridae and more preferably infections with Bovine Viral Diarrhea virus (BVDV).

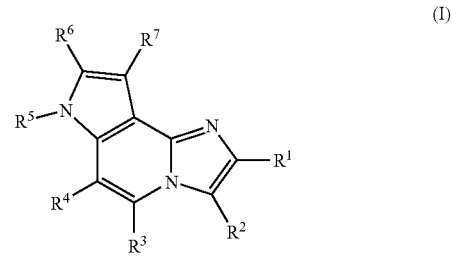

(I)

5 Claims, No Drawings

IMIDAZO [1, 2-A] PYRROLO [3, 2-C] PYRIDINE COMPOUNDS USEFUL AS PESTIVIRUS INHIBITORS

CROSS-REFERENCE TO RELATED APPLICATIONS

This application is the national stage of International Application No. PCT/BE2007/000127, filed Dec. 14, 2007, which claims benefit of British Application No. GB 0624983.3, filed Dec. 14, 2006.

FIELD OF THE INVENTION

The present invention relates to a series of novel imidazo [1,2-a]pyrrolo[3,2-c]pyridines (or also named 6H-1,3a,6-Triaza-as-indacenes) and derivatives thereof, processes for their preparation, their use as a medicine, their use to treat or prevent viral infections and their use to manufacture a medicine to treat or prevent viral infections, particularly infections with viruses belonging to the family of the Flaviviridae and more preferably infections with Bovine Viral Diarrhea virus (BVDV).

BACKGROUND OF THE INVENTION

The family of the Flaviviridae consists of 3 genera, the pestiviruses, the flaviviruses and the hepaciviruses and also contains the hepatitis G virus (HGV/GBV-C) that has not yet been assigned to a genus.

Pestiviruses such as the Classical Swine Fever Virus (CSFV), the Bovine Viral Diarrhea Virus (BVDV) and the Border Disease Virus (BDV) cause infections of domestic livestock (respectively pigs, cattle and sheep) and are responsible for significant economic losses world-wide. BVDV, the prototypic representative of the pestivirus genus is ubiquitous and causes a range of clinical manifestations, including abortion, teratogenesis, respiratory problems, chronic wasting disease, immune system dysfunction, and predisposition to secondary viral and bacterial infections and may also cause acute fatal disease. Foetuses of cattle can be infected persistently with BVDV, these animals remain viremic throughout life and serve as a continuous sources for virus spread in herds.

Vaccines are used in some countries with varying degrees of success to control pestivirus disease. In other countries, animal culling and slaughter are used to contain pestivirus disease outbreaks.

The compound 3-[((2-dipropylamino)ethyl)thio]-5H-1,2,4-triazino[5,6-b]indole (VP32947) has been reported to selectively inhibit the replication of BVDV and other pestiviruses (Baginski S G and al., Proc. Natl. Acad. Sci. U.S.A. 2000 Jul. 5; 97(14):7981-6). Also 5-[(4-bromophenyl)methyl]-2-phenyl-5H-imidazo[4,5-c]pyridine (BPIP), has recently been described as possessing potent anti-pestivirus activity. Currently, there is no treatment strategy available on the market for controlling infections caused by pestiviruses.

Therefore, there is a need for novel, potent compounds which show antiviral activity against Flaviviridae, more specifically against Pestiviruses.

The present invention provides for novel compounds which show activity against viruses, more specifically against Flaviviridae. There is a clear need in the field for alternative antiviral compounds, furthermore with a good activity vs toxicity profile and this specifically for the viruses of the family of the Flaviviridae, more specifically for Pestiviruses.

The prior art does not lead a person skilled in the art to the compounds of the present invention and to their use as antiviral compounds.

SUMMARY OF THE INVENTION

Herein we provide that imidazo[1,2-a]pyrrolo[3,2-c]pyridines (6H-1,3a,6-triaza-as-indacenes) exhibit potent inhibition effects on Flaviridae, more specifically Pestiviruses, yet more specifically on BVDV. Cytotoxicity was found low for these compounds.

In the present invention, new selective anti-viral compounds are being provided. The compounds are imidazo[1,2-a]pyrrolo[3,2-c]pyridines and it has been shown that they possess an anti-viral activity. Members of the Flaviviridae family are being inhibited. The present invention demonstrates that the compounds inhibit the replication of BVDV. Therefore, these imidazo[1,2-a]pyrrolo[3,2-c]pyridines constitute a new potent class of anti-viral compounds that can be used in the treatment and prevention of viral infections in animals, mammals and humans, more specifically for the treatment and prevention of Flaviviridae, more specifically of BVDV.

The present invention relates to imidazo[1,2-a]pyrrolo[3,2-c]pyridines. The invention further relates to compounds having anti-viral activity, more specifically to imidazo[1,2-a]pyrrolo[3,2-c]pyridines that inhibit the replication of viruses. Most particularly, the invention relates to imidazo[1,2-a]pyrrolo[3,2-c]pyridines which inhibit the replication of viruses of the family of the Flaviviridae and yet more specifically to compounds that inhibit the replication of BVDV (Bovine Viral Diarrhea Virus) infections. Present invention furthermore relates to the compounds for use as a medicine and to the use of the compounds as a medicine, more specifically to use the compounds as an anti-viral. The invention also relates to methods for preparation of all such compounds and pharmaceutical compositions comprising them. The invention further relates to the use of said compounds in the manufacture of a Medicament useful for the treatment of viral infections, more specifically of Pestivirus infections. The present invention also relates to a method of treatment of viral infections, by using said compounds.

According to a first aspect, the invention relates to imidazo [1,2-a]pyrrolo[3,2-c]pyridines and derivatives thereof, which according to the general embodiment of the invention correspond to compounds according to the general formula (I), pharmaceutically acceptable salts, solvates, tautomers and isomers (particularly stereoisomers) thereof,

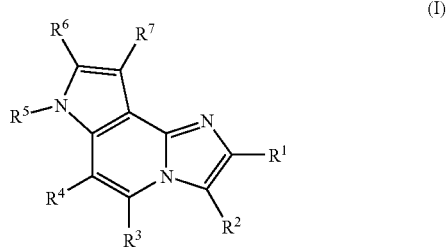

(I)

wherein:
each of $R^1$, $R^2$, $R^6$ and $R^7$ are independently selected from hydrogen; —OH; —SH; —NH$_2$; —NO$_2$; halogen; or a $C_{1-16}$ hydrocarbyl group which optionally includes one or more heteroatoms at any position of the hydrocarbyl group (in the main or side chains), said heteroatoms being selected from the groups consisting of O, S, and N and wherein said hydrocarbyl group can be unsubstituted or substituted with one or more $Z^1$;

$R^5$ is independently selected from hydrogen; or a $C_{1-16}$ hydrocarbyl group which optionally includes one or more heteroatoms at any position of the hydrocarbyl group (in the main or side chains), said heteroatoms being selected from the groups consisting of O, S, and N and wherein said hydrocarbyl group can be unsubstituted or substituted with one or more $Z^1$;

$Z^1$ is independently selected from the group consisting of —OH; —SH; —$NH_2$; halogen; —$OCF_3$; —$NO_2$; or a $C_{1-16}$ hydrocarbyl group which optionally includes one or more heteroatoms at any position of the hydrocarbyl group (in the main or side chains), said heteroatoms being selected from the groups consisting of O, S, and N;

In a particular embodiment, the invention relates to imidazo[1,2-a]pyrrolo[3,2-c]pyridines and derivatives thereof, which correspond to compounds according to the general formula (II), pharmaceutically acceptable salts, solvates; tautomers and isomers (particularly stereoisomers) thereof,

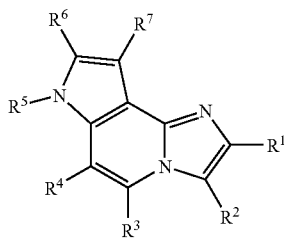

(II)

wherein:
each of $R^1$, $R^2$, $R^3$, $R^4$, $R^6$ and $R^7$ are independently selected from hydrogen; —OH; —SH; —$NH_2$; —$NO_2$; —CN; —$OCF_3$; —$NZ^2Z^3$; C(=O)$Z^4$; C(=S)$Z^4$; halogen; tri-$C_{1-16}$-alkylsilyl; $C_{1-16}$ alkyl (including haloalkyl), preferably $C_{1-6}$ alkyl; $C_{2-16}$ alkenyl; $C_{2-16}$ alkynyl; $C_{1-16}$ alkoxy, preferably $C_{1-6}$ alkoxy; $C_{1-16}$ alkylthio; $C_{3-16}$ cycloalkyl; $C_{4-16}$ cycloalkenyl; $C_{4-16}$ cycloalkynyl; aryl; aryloxy; arylthio; arylalkyl; heterocycle; oxyheterocycle; thioheterocycle; and each of said alkyl, alkenyl, alkynyl, alkoxy, alkylthio, cycloalkyl, cycloalkenyl, cycloalkynyl, aryl, aryloxy, arylthio, arylalkyl, heterocycle; oxyheterocycle; thioheterocycle can be substituted with 1 or more $Z^1$;

$R^5$ is independently selected from hydrogen; C(=O)$Z^4$; C(=S)$Z^4$; $C_{1-16}$ alkyl (including haloalkyl), preferably $C_{1-6}$ alkyl; $C_{2-16}$ alkenyl; $C_{2-16}$ alkynyl; $C_{1-16}$ alkoxy, preferably $C_{1-6}$ alkoxy; $C_{1-16}$ alkylthio; $C_{3-16}$ cycloalkyl; $C_{4-16}$ cycloalkenyl; $C_{4-16}$ cycloalkynyl; aryl; aryloxy; arylthio; arylalkyl; heterocycle; oxyheterocycle; thioheterocycle; and each of said alkyl, alkenyl, alkynyl, alkoxy, alkylthio, cycloalkyl, cycloalkenyl, cycloalkynyl, aryl, aryloxy, arylthio, arylalkyl, heterocycle; oxyheterocycle; thioheterocycle can be substituted with 1 or more $Z^1$;

$Z^1$ is independently selected from the group consisting of —OH; —SH; —$NH_2$; —$NO_2$; —CN; —$OCF_3$; —$NZ^2Z^3$; C(=O)$Z^4$; C(=S)$Z^4$; halogen; $C_{1-16}$ alkyl (including haloalkyl), preferably $C_{1-6}$ alkyl; $C_{2-16}$ alkenyl; $C_{2-16}$ alkynyl; $C_{1-16}$ alkoxy, preferably $C_{1-6}$ alkoxy; $C_{1-16}$ alkylthio; $C_{3-16}$ cycloalkyl; $C_{4-16}$ cycloalkenyl; $C_{4-16}$ cycloalkynyl; aryl; aryloxy; arylthio; arylalkyl; heterocycle; oxyheterocycle; thioheterocycle;

each $Z^2$ and $Z^3$ is independently selected from hydrogen; $C_{1-16}$ alkyl, preferably $C_{1-6}$ alkyl;

$Z^4$ is selected from hydrogen; OH; $C_{1-16}$ alkyl; $C_{1-16}$ alkoxy; $NZ^2Z^3$; aryl.

In another particular embodiment, each of $R^3$ and $R^4$ are hydrogen. As such, the present invention therefore relates to imidazo[1,2-a]pyrrolo[3,2-c]pyridines according to the formula III, pharmaceutically acceptable salts, solvates, tautomers and isomers (particularly stereoisomers) thereof

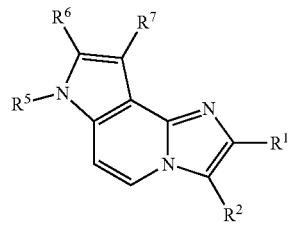

(III)

wherein each of $R^1$, $R^2$, $R^5$, $R^6$ and $R^7$ are as described in formula I, in a more particular embodiment as in formula II.

In a more particular embodiment the present invention relates to compounds according to formula III, wherein
$R^1$ is selected from hydrogen; halogen; $C_{1-16}$ alkyl (including haloalkyl), preferably $C_{1-6}$ alkyl; $C_{1-16}$ alkoxy, preferably $C_{1-6}$ alkoxy; aryl; aryloxy; arylalkyl; and each of said alkyl, alkoxy, aryl, aryloxy and arylalkyl can be substituted with 1 or more $Z^1$;
$R^2$ is selected from hydrogen; halogen and —$NO_2$;
$R^5$ is selected from hydrogen and —C(=O)$Z^4$;
$R^6$ is selected from aryl; $C_{1-16}$ alkyl (preferably $C_{1-6}$ alkyl) and —C(=O)$Z^4$;
$R^7$ is selected from $C_{1-16}$ alkyl preferably $C_{1-6}$ alkyl;
$Z^1$ is independently selected from the group consisting of $C_{1-16}$ alkyl (including haloalkyl), preferably $C_{1-6}$ alkyl; $C_{1-16}$ alkoxy, preferably $C_{1-6}$ alkoxy; halogen; —OH; —$NZ^2Z^3$; aryl; aryloxy; arylalkyl;
each $Z^2$ and $Z^3$ is independently selected from hydrogen; $C_{1-16}$ alkyl, preferably $C_{1-6}$ alkyl; aryl, preferably phenyl;
$Z^4$ is selected from hydrogen; OH; $C_{1-16}$ alkyl; $C_{1-16}$ alkoxy; $NZ^2Z^3$; aryl; and aryloxy.

In a particular embodiment of the present aspect, the imidazo[1,2-a]pyrrolo[3,2-c]pyridines of the present invention do not comprise the following compounds:
compounds according to the formulas herein wherein $R^2$ is —$NH_2$ or in a particular embodiment is a substituted amine such as $NZ^2Z^3$ such as the compounds described in EP0822194 and the patent applications and patents belonging to family of EP0822194 (especially compounds 290, 291, 292, 293, 294, 295, 296, 297, 298, 299, 300, 301, 302, 332 or 344 in EP0822194); and/or
compounds according to the formulas herein wherein $R^7$ is a substituted C(=O), such as in C(=O)$Z^4$ or C(=S)$Z^4$, such as the compounds described in WO02/12442 and the patent applications and patents belonging to family of WO02/12442 (especially compounds according to formula II in WO02/12442); and/or
imidazo[1,2-a]pyrrolo[3,2-c]pyridine (as in Chezal and al., J. Org. Chem. 2001, 66, 6576-6584); and/or ethyl 2-bromoimidazo[1,2-a]pyrrolo[3,2-c]pyridine-8-carboxylate (or also named 2-bromo-6H-1,3a,6-triaza-as-indacene-7-carboxylic acid ethyl ester) (as in Chezal and al., J. Org. Chem. 2001, 66, 6576-6584); and/or ethylimidazo[1,2-a]pyrrolo[3,2-c]pyridine-8-carboxylate (as in Chezal and al., J. Org. Chem. 2001, 66, 6576-6584).

A second aspect of the present invention relates to the compounds according to formulas I, II and III and embodiments thereof for use as a medicine.

Another aspect of the present invention relates to the use of compounds according to formulas I, II and III, pharmaceutically acceptable salts, tautomers, and isomers thereof for the manufacture of a medicament, or a pharmaceutical composition having antiviral activity, to treat or prevent viral infections in a mammal, more in particular Flaviviral infections.

The present invention further relates to the use of the compounds according to formulas I, II or III above as a medicine and to the use of such compounds in the treatment or prevention of a viral infection in a mammal.

In a particular embodiment, said viral infection is an infection with an RNA-virus, yet more in particular with a virus of the family of the Flaviviridae. Yet more in particular, said viral infection is an infection with Bovine viral diarrhea virus (BVDV) or Hepatitis C virus (HCV).

In another particular embodiment, said mammal in need of treatment or prevention of a viral infection is cadle or human.

The invention also relates to the use of the compounds according to formula I, II and III above as a pharmaceutically active ingredient, especially as an inhibitor of the viral replication, more preferably as an inhibitor of the replication of a virus of the family of the Flaviviridae and yet more preferably as an inhibitor of the replication of BVDV.

The present invention further relates to a method of treatment of a viral infection in a mammal, including caddie and humans, comprising administering to the mammal in need of such treatment (a therapeutically effective amount of) a compound according to formula I, II or III above as an active ingredient, optionally in a mixture with at least a pharmaceutically acceptable carrier.

Another aspect of the present invention relates to a pharmaceutical composition comprising one or more compounds according to formulas and embodiments above, in admixture with at least one pharmaceutically acceptable carrier.

The present invention further relates to a composition for separate, combined or sequential use in the treatment or prophylaxis of anti-viral infections, comprising:
a) one or more of the, and
b) one or more compounds effective in the treatment or prophylaxis of viral infections, including Flaviviral enzyme inhibitors; in proportions such as to provide a synergistic effect in the said treatment of prophylaxis.

The invention further relates to methods for the preparation of the compounds according to formulas as detailed above, more particularly to methods for the preparation of the compounds specifically disclosed herein, to pharmaceutical compositions comprising them in admixture with at least a pharmaceutically acceptable carrier, the active ingredient optionally being in a concentration range of, about 0.1-100% by weight, and to the use of these derivatives namely as antiviral drugs, more particularly as drugs useful for the treatment of subjects suffering from HCV infection.

The invention also relates to a method for preparing the compounds according to the formulas above and embodiments thereof as described herein.

One of such a method comprises the steps of:
a) reacting a solution of a substituted or unsubstituted alkyl 2-aminopyridine-3-carboxylate with a halogenated ketone or aldehyde in the form of XR' CHCOR", wherein X is a halogen and R', R" can be selected from different groups including, but not limited to hydrogen and unsubstituted or substituted alkyl and aryl except when R'=R"=H.
b) forming the alkyl carboxylate into the corresponding aldehyde through the use of reducing and/or oxidation reagents
c) conversion of the aldehydes obtained in the previous steps to the azidoethylpropenoate by using ethylazidoacetate and subsequently form the imidazo[1,2-a]pyrrolo[3,2-c]pyridine ring system by cyclisation.

The present invention also provides an alternative method for the preparation of the compounds according to the formulas above and embodiments thereof as described herein, such a method comprises the steps of:
a) reacting a solution of 2,4-diamino-3-halogenopyridine, preferentially 2,4-diamino-3-bromo or 3-iodopyridine, with a halogenated ketone or aldehyde in the form of XR'CHCOR", wherein X is a halogen and R', R" can be selected from different groups including, but not limited to hydrogen and unsubstituted or substituted alkyl and aryl except when R'=R"=H.
b) Incorporating or not suitable amino protecting groups into the molecule.
c) Formation of the imidazo[1,2-a]pyrrolo[3,2-c]pyridine ring system via palladium or copper catalyzed annulation of alkynes or enamines. At this step, the protecting group can then be removed to regenerate the original function.

According to a particular embodiment, the present invention relates to compounds selected from the group of compounds specified in the tables in the application, the pharmaceutically acceptable salts, tautomers, and isomers (especially steroisomers) thereof and their use in a treatment of viral infection or to manufacture a medicament to treat viral infections.

DETAILED DESCRIPTION OF THE INVENTION

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The terms mentioned herein with, prefixes as $C_{1-16}$ can also be used with lower numbers of carbon atoms such as $C_{1-8}$ or $C_{1-6}$. If for example the term $C_1$-$C_6$ is used, it refers to the presence of between 1 and 6 carbon atoms.

The term "one or more" can refer to 1 to 100, in a particular embodiment to 1 to 50, in another particular embodiment to 1 to 30, yet more particularly to 1 to 20, and in a still more particular embodiment to 1 to 10 and includes all numbers between the given ranges, such as for 1 to 20, contains 1, 2, 3, 4, 5, 6, 7, 8, 9, 10, 11, 12, 13, 14, 15, 16, 17, 18, 19 and 20.

The term "$C_1$-$C_{16}$ hydrocarbyl, group" as used herein refers to $C_1$-$C_{16}$ normal, secondary, tertiary unsaturated or saturated, acyclic, cyclic or aromatic hydrocarbons and combinations thereof. The term therefore comprises alkyl, alkenyl, alkynyl, cycloalkyl, cycloalkenyl, cycloalkynyl, aryl, arylalkyl, arylalkenyl, arylalkynyl, alkylaryl, alkenylaryl, alkynylaryl, alkylcycloalkyl, alkylcylcoalkenyl and alkenyl-cycloalkyl among others. When referring to a "hydrocarbyl group which optionally includes one or more heteroatoms at any position of the hydrocarbyl group (in the main or side chains), said heteroatoms being selected from the groups consisting of O, S, and N", refers to a hydrocarbyl group wherein one or more carbon atoms of said hydrocarbyl group can be replaced by a heteroatom which is coupled via single, double or triple bonds and than at least comprises one carbon atom. This terminology thus can comprise hydrocarbyl groups with carbonyl, thienyl, imine or nitrile groups. This thus includes alkoxy such as methoxy, hydroxy-alkylene such as hydroxymethylene (—CH$_2$OH), —CN, alkyl-CN, —COOH, —COOalkyl, alkylCOOH, NHalkyl, NHalkenyl, N(alkyl)$_2$, alkylNHalkyl, C(=O)alkyl, C(=S)alkyl, alkylthio, alkyl-O-alkyl, alkyl-S-alkyl, alkenyl-O-alkyl, aryloxy, arylthio, arylalkoxy, benzoyl, heterocycle, heterocycle-alkyl, heterocycle-alkoxy, among others.

The term "$C_{1-16}$ alkyl" as used herein refers to $C_1$-$C_{16}$ normal, secondary, or tertiary unsaturated hydrocarbon. Examples are methyl, ethyl, 1-propyl, 2-propyl, 1-butyl, 2-methyl-1-propyl (i-Bu), 2-butyl (s-Bu), 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl; 2,3-dimethyl-2-butyl, 3,3-dimethyl-2-butyl, cyclopropyl, cyclobutyl, cyclopentyl and cyclohexyl. In a particular embodiment, the term also includes $C_{1-16}$ haloalkyls, which is a $C_{1-16}$ alkyl bearing at least one halogen.

As used herein and unless otherwise stated, the term "$C_{3-16}$ cycloalkyl" means a monocyclic saturated hydrocarbon monovalent radical having from 3 to 16 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein and unless otherwise stated, the term "$C_{3-16}$ cycloalkylene" refers to a cyclic hydrocarbon radical of 3-16 carbon atoms, and having two monovalent radical centers derived by the removal of two hydrogen atoms from the same or two different carbon atoms of a parent alkane; i.e. the divalent hydrocarbon radical corresponding to the above defined $C_{3-16}$ cycloalkyl.

The terms "$C_{2-16}$ alkenyl" and "$C_{3-10}$ cycloalkenyl" as used herein is $C_2$-$C_{16}$ normal, secondary or tertiary and respectively $C_{3-16}$ cyclic hydrocarbon with at least one site (usually 1 to 3, preferably 1) of unsaturation, i.e. a carbon-carbon, sp2 double bond. Examples include, but are not limited to: ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$). The double bond may be in the cis or trans configuration.

The terms "$C_{2-16}$ alkynyl" and "$C_{3-16}$ cycloalkynyl" as used herein refer respectively $C_2$-$C_{16}$ normal, secondary, tertiary or the $C_{3-16}$ cyclic hydrocarbon with at least one site (usually 1 to 3, preferably 1) of unsaturation, i.e. a carbon-carbon, sp triple bond. Examples include, but are not limited to: acetylenyl (—C≡CH) and propargyl (—CH$_2$C≡CH).

The terms "$C_{1-16}$ alkylene" as used herein each refer to a saturated, branched or straight chain hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

The terms "$C_{2-16}$ alkenylene" and "$C_{3-16}$ cycloalkenylene" as used herein refer to an unsaturated branched chain, straight chain, and respectively a cyclic hydrocarbon radical of 2-16 respectively 3-16 carbon atoms, and having two monovalent radical centers derived by the removal of two hydrogen atoms from the same or two different carbon atoms of a parent alkene, i.e. double carbon-carbon bond moiety. Typical alkenylene radicals include, but are not limited to: 1,2-ethylene (—CH=CH—).

The terms "$C_{2-16}$ alkynylene" and "$C_{3-16}$ cycloalkynylene" as used herein refer respectively to an unsaturated, branched or straight chain of 2-16 carbon atoms or to a cyclic hydrocarbon radical of 3-16 carbon atoms respectively, having two monovalent radical centers derived by the removal of two hydrogen atoms from the same or two different carbon atoms of a parent alkyne, i.e. triple carbon-carbon bond moiety. Typical alkynylene radicals include, but are not limited to: acetylenyl (—C≡C—), propargyl (—CH$_2$C≡C—), and 4-pentynyl (—CH$_2$CH$_2$CH$_2$C≡CH—).

The term "aryl" as used herein means a mono- or polycyclic aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, spiro, anthracene, biphenyl, and the like.

"Arylalkyl" as used herein refers to an alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl; 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

The term "heterocycle" as used herein means a mono- or polycyclic, saturated or mono-unsaturated or polyunsaturated monovalent hydrocarbon group having from 3 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic groups such as, but not limited to pyridyl, 2H-chromenyl, dihydropyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

Heteroaryl means pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

By way of example, carbon bonded heterocycle are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocycle are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, 1-piperidinyl.

The term protecting groups for the functional amino group discussed above are described in Greene and Wuts, "Protective Groups in Organic synthesis", John Wiley & Sons (1991), the entire teachings of which are incorporated into this application by reference. The person skilled in the art can select, using no more than routine experimentation, suitable protecting groups for use in the disclosed synthesis, including protecting groups other than those described below, as well as conditions for applying and removing the protecting groups. Example of suitable amino protecting groups include aryloxy and alkyloxycarbonyl, tert-butyl, benzyl and fluorenylethyloxycarbonyl.

"Carbocycle" means a saturated, unsaturated or aromatic ring system having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. Carbocycle thus includes some aryl groups.

As used herein and unless otherwise stated, the terms "$C_{1-16}$ alkoxy", "$C_{3-16}$ cycloalkoxy", "aryloxy", "arylalkyloxy", "oxyheterocyclic ring", "thio $C_{1-16}$ alkyl", "thio $C_{3-16}$ cycloalkyl", "arylthio", "arylalkylthio" and "thioheterocyclic ring" refer to substituents wherein a $C_{1-16}$ alkyl radical, respectively a $C_{3-16}$ cycloalkyl, aryl, arylalkyl or heterocyclic ring radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like.

As used herein and unless otherwise stated, the term halogen means any atom selected from the group consisting of fluorine, chlorine, bromine and iodine.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

It has been shown in the present invention that novel imidazo[1,2-a]pyrrolo[3,2-c]pyridines show potent antiviral activity.

This invention provides several synthetic methodologies for creating imidazo[1,2-a]pyrrolo[3,2-c]pyridine derivatives according to the following general procedures exemplified with some specific imidazo[1,2-a]pyrrolo[3,2-c]pyridines. These procedures can however be applied by a person skilled in the art to other compounds of the invention.

1/Synthesis Method 1

In a first step, alkyl imidazo[1,2-a]pyridine-8-carboxylates (for example ethyl imidazo[1,2-a]pyridine-8-carboxylates) were formed by reacting a solution of a substituted or unsubstituted alkyl 2-aminopyridine-3-carboxylate (according to Zhou, Z. L. and al. Bioorg. Med. Chem. 2001, 9, 2061-2071) in an appropriate solvent with a halogenated ketone or aldehyde in the form of XR'CHCOR", wherein X is a halogen and R', R" can be selected from different groups including, but not limited to hydrogen and unsubstituted or substituted alkyl and aryl except when R'=R"=H. When R'=CHCl$_2$ (as exemplified in Scheme 1) condensation reaction must be performed in two steps using, in the first step, aprotic solvent such 1,2-dimethoxyethane (DME) and at room temperature to afford a salt which is filtered to eliminate excess of 1,1,3-trichloracetone. In the final step, this salt is refluxed in ethanol to give a mixture of dichloro compound 2h and ketal 2i. Compound 2h is easily converted into 2i using an organic base, preferentially 4-dimethylaminopyridine, in refluxing anhydrous ethanol. The starting material can comprise substituents such as alkyl so that the positions $R^3$ and $R^4$ are substituted (as an example alkyl 5- or 6-methyl-2-aminopyridine-3-carboxylate). In a following step to convert alkyl carboxylate 2 to alcohol 3 a reducing agent can be used, e.g. sodium borohydride, lithium aluminium hydride (LAH) and the like. A preferred reducing agent is LAH in the presence of tetrahydrofuran (THF). Subsequently, the formed alcohol 3 is oxidized to the corresponding aldehyde, for example by applying manganese(IV) oxide in refluxing solvent. A preferred solvent for this reaction is a nonpolar volatile solvent such as chloroform.

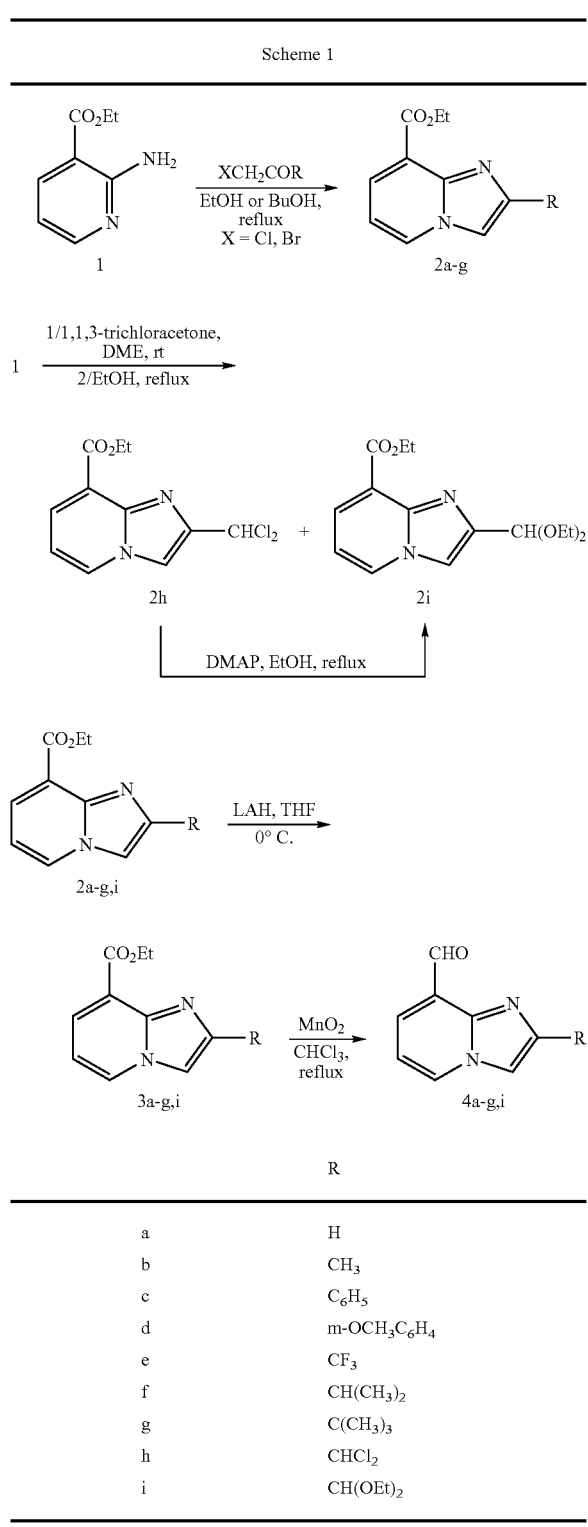

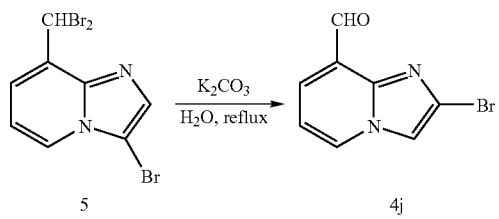

Substituents on $R^2$ position, the most reactive site for electrophilic aromatic substitution reactions in imidazo[1,2-a] pyridinic series, can be introduced at this stage by using different reactions such as halogenation or nitration. For example, bromination of compounds 4a, b using bromine in acidic media, such acetic acid, affords 3-bromo derivatives 4k, l. Using a similar way, nitration of compound 4b with a sulfuric-nitric acid mixture, gives 3-nitro compound 4m (Scheme 3).

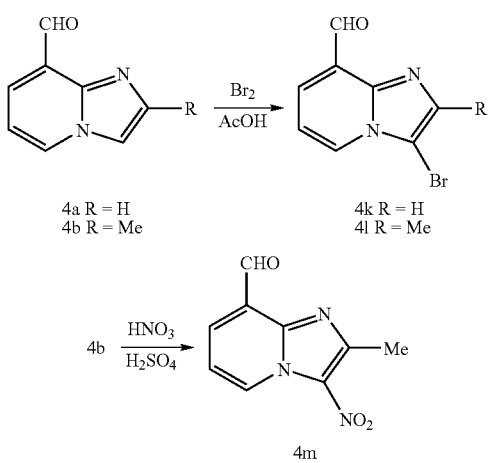

In order to obtain the imidazo[1,2-a]pyrrolo[3,2-c]pyridine ring system, the aldehydes 4 obtained in the previous steps can be converted to the ethyl azidopropenoates 6 by using ethyl azidoacetate, which can subsequently be cyclized by refluxing in an appropriate solvent, such as chlorobenzene, as set forth below in Scheme 4. For the synthesis of azides 6 the reaction must be carried out at −30° C. and with limited quantities of 4 (<10 mmoles) to prevent explosion hazards. Typically the reaction is conduced with 14 equivalents of ethyl azidoacetate per mole of 4. Lower concentrations of ethyl azidoacetate yield only starting material.

For the synthesis of compounds of the invention with a 2-halogenoimidazo[1,2-a]pyridine-8-carbaldehyde structure such as compound 4j, the known reaction was used as described in Chezal, J. M. and al. J. Org. Chem. 2001, 66, 6576-6584. Isomerisation of the halogenated group in the 2-position results of a classical Dimroth rearrangement (Scheme 2).

Scheme 4

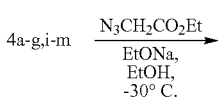

Scheme 4 (continued)

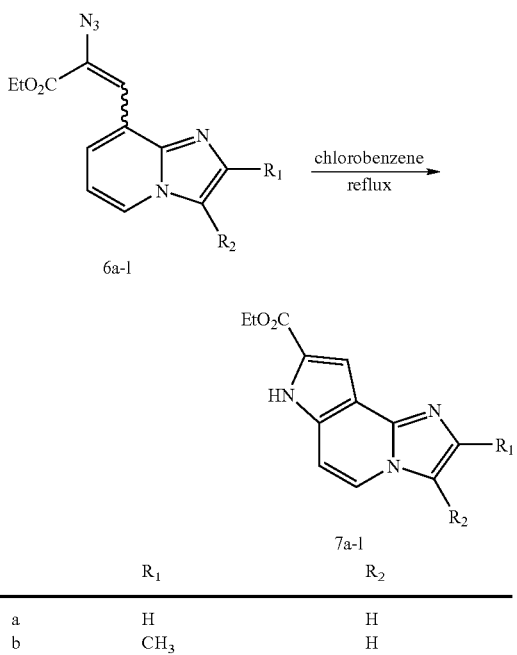

| | $R_1$ | $R_2$ |
|---|---|---|
| a | H | H |
| b | $CH_3$ | H |
| c | $C_6H_5$ | H |
| d | $m\text{-}OCH_3C_6H_4$ | H |
| e | $CF_3$ | H |
| f | $CH(CH_3)_2$ | H |
| g | $C(CH_3)_3$ | H |
| h | $CH(OEt)_2$ | H |
| i | Br | H |
| j | H | Br |
| k | $CH_3$ | Br |
| l | $CH_3$ | $NO_2$ |

Finally, substituents on different positions of the imidazo [1,2-a]pyrrolo[3,2-c]pyridine ring such as $R^1$, $R^5$ and $R^6$ can be introduced or changed with different process, such as exemplified in schemes 5, 6 and 7.

As depicted in Scheme 5, ketal 7h can be hydrolysed using mild conditions to afford carboxaldehyde 8. The reaction may be conveniently effected using catalytic acidic conditions, such as hydrochloric acid, in a mixture of 3/1, v/v acetonitrile/water and at room temperature. Reductive amination of carbaldehyde 8, via imine, gives amine 9. In a preferred embodiment, carbaldehyde 8 can be react with hydrohalide amine salt, such as dimethylamine hydrochloride salt, in the presence of a base such as an organic base, e.g. triethylamine, an appropriate solvent such methanol, and at room temperature. The resulting imine is then reduced preferentially with sodium cyanoborohydride and at room temperature to afford amine 9.

Scheme 5

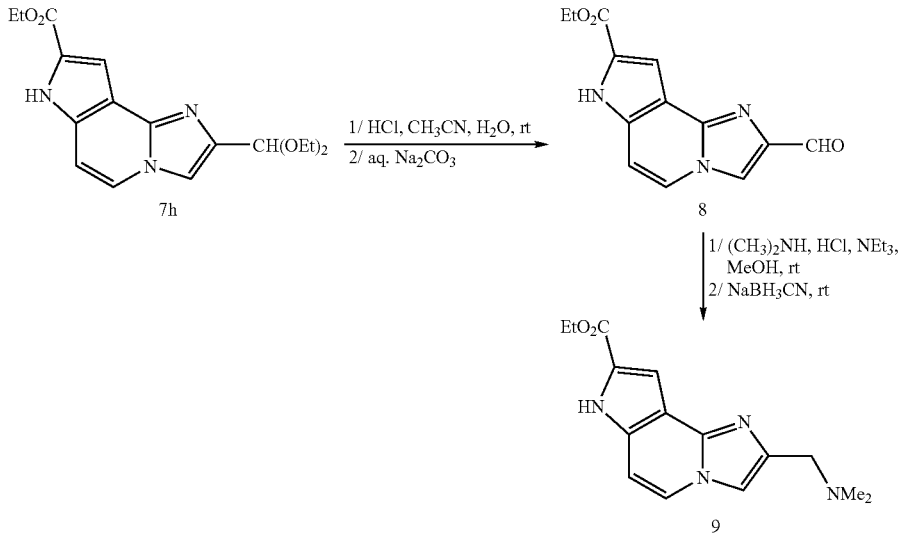

The carboxylic ester or carbaldehyde groups can be reduced to hydroxymethyl derivatives with a suitable reducing agent in an inert solvent. For example, as described in scheme 6, ethyl ester 7i is converted in alcohol 10 with diisobutylaluminum hydride (DIBAL-H), in aprotic apolar solvent, such as dichloromethane, and at low temperature preferentially at −80° C. Using a similar way, carboxaldehyde 8 is reduced selectively in hydroxymethyl 11 with sodium borohydride in an inert solvent, such as ethanol, and at room temperature. The alcohol previously obtained can also be converted in corresponding halomethyl using a halogenating reagent. For example, compound 11 reacts with thionyl chloride in the presence of an organic base, such as trimethylamine, an inert solvent, such as dichloromethane, and at room temperature to afford chloromethyl 12.

Scheme 6

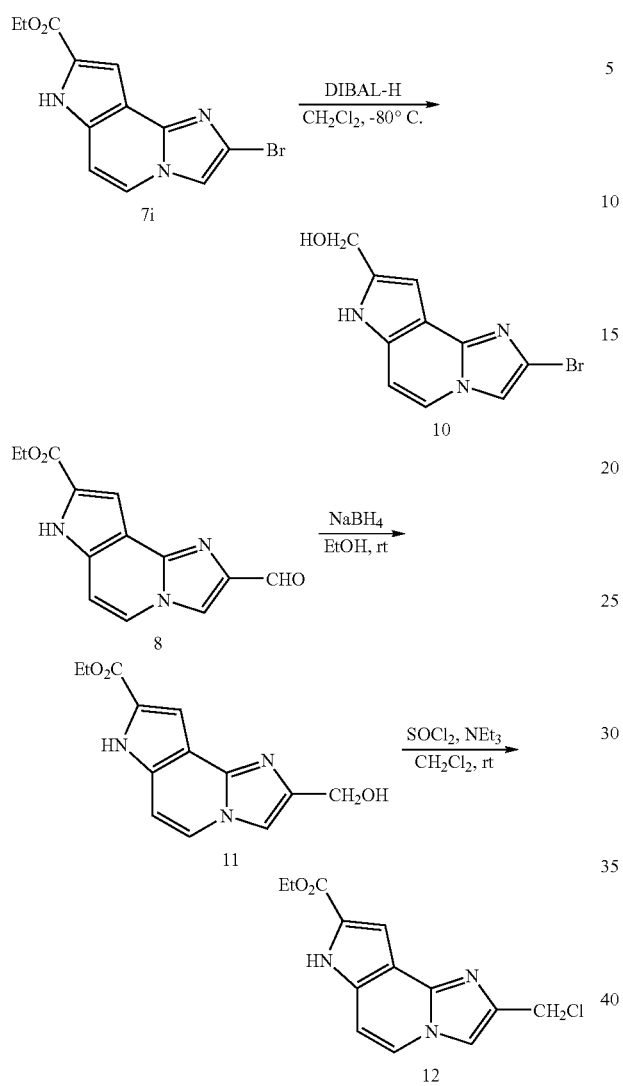

sis of compound 7b followed by carefully acidication with concentrated hydrochloric acid affords acid 15. In a preferred embodiment potassium hydroxyde solution is employed with a mixture of 1/1, v/v ethanol/THF solution and at room temperature. Esterification of acid 15 with an anhydrous alcohol in the presence of acidic catalyst or a halogenating reagent gives esters 16.

Halogenating reagents for the above reaction include those which can convert carboxylic acid to an acid halide, e.g. thionyl chloride, phosphorus trichloride, phosphorus pentachloride and the like. A preferred halogenating reagent is thionyl chloride in the presence of DMF. After conversion of acid 15 to the acid halide, the alcohol can be condensed in the presence of an organic base such as triethylamine. Acidic catalyst for the above reaction includes hydrogene halide, sulfuric acid and the like. A preferred acidic catalyst is hydrogene chloride gas with a small quantity of concentrated sulfuric acid. Anhydrous alcohols include aryl and alkyl alcohols phenol, methanol, propanol, butanol and the like.

Scheme 7

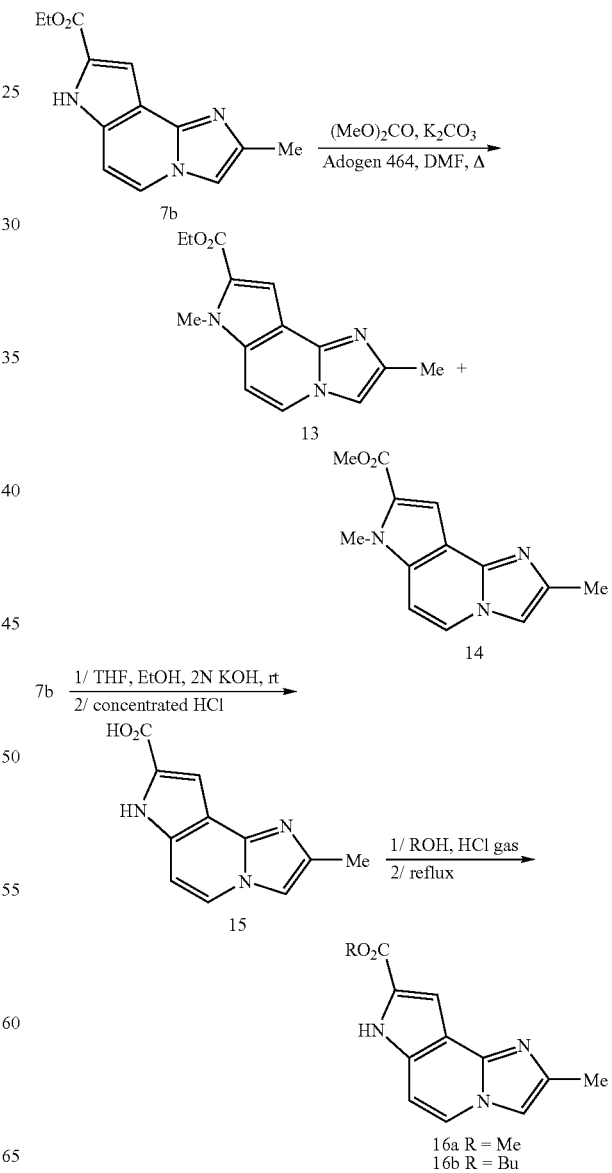

Substituent in $R^5$ position can be introduced using suitable alkylating conditions, such as from N-unsubstituted pyrrole derivatives using an appropriate alkylating agent, such as alkylhalide, arylalkylhalide or dimethyl carbonate, in the presence of a base, preferentially an inorganic base, such potassium carbonate, sodium hydride or potassium hydroxide, with or without a phase transfert catalyst, e.g. adogen 464, and an appropriate solvent, such a mixture of water/dichloromethane or dry polar aprotic solvent such as acetonitrile, dimethylformamide (DMF) or dimethylsulfoxide (DMSO) and at the appropriate temperature. For example, as described in Scheme 7, alkylation of compound 7b gives compound 13 with an appropriate alkylating agent, such as dimethyl carbonate, in the presence of a base, preferentially an inorganic base, such potassium carbonate, a phase transfert catalyst, e.g. adogen 464, and an appropriate solvent, such a mixture of water/dichloromethane or dry dimethylformamide (DMF), and at an elevated temperature. During this synthesis a trans-esterification reaction occurs to afford methyl ester compound 14 which is isolated by alumina chromatography. A more convenient methodology, in two steps, can be used to obtain various aryl or alkyl esters from ethyl carboxylate esters 7. As depicted in Scheme 7, ester hydroly-

2/Synthesis Method 2

By addition of a halogenated ketone or aldehyde in the form of XR'CHCOR", wherein X is a halogen and R', R" can be selected from different groups including, but not limited to hydrogen and unsubstituted or substituted alkyl and aryl except when R'=R"=H, to a solution of 2,4-diamino-3-halogenopyridine according to Rauckman B. S. and al. J. Med. Chem. 1980, 23, 384-391 in an appropriate solvent. Preferentially the reaction is carried out with 2,4-diamino-3-bromopyridine or 2,4-diamino-3-iodopyridine. For example 2,4-diamino-3-bromopyridine reacts with chloracetone in refluxing ethanol 17 to give 7-amino-8-bromo-2-methylimidazo[1,2-a]pyridine 18 as depicted in scheme 8.

In order to optimize the conditions of the palladium catalyzed reactions also call Larock or Sonogashira procedure (Humphrey, G. R. and al. Chem. Rev. 2006, 106, 2875-2911) and to obtain better yields, the amine may have to be protected, as is known in the art, and the protecting group could be removed following the coupling reaction. The process is carried out in a manner known. As carbonic acid derivative preferably the corresponding alkyl chloroformates or di-alkyl-dicarbonates can be used. The methoxycarbonyl, ethoxycarbonyl and benzyloxycarbonyl group may be preferably introduced with the aid of methyl chloroformate, ethyl chloroformate and benzyl chloroformate, respectively. The tertiary butoxycarbonyl group may be introduced preferably by using di-tertbutyldicarbonate. As alkanoyl derivative preferably the corresponding carboxylic acid halide or carboxylic acid anhydride can be used. The ethanoyl, trifluoroethanoyl, propanoyl and butanoyl may be preferably introduced with the aid of ethanoyl chloride or ethanoic anhydride, trifluoroethanoyl chloride or trifluoroethanoic acid anhydride, propionyl chloride or propionic anhydride, butyryl chloride or butanoic anhydride, respectively. The acylation reaction is carried out in an inert organic solvent and in the presence of an inorganic and/or organic base. As inert organic solvent preferably halogenated aliphatic hydrocarbons (e.g. dichloromethane, dichloroethane or chloroform), esters (e.g. ethyl acetate) or ketones (e.g. acetone), can be used. As inorganic base preferably alkali carbonates (e.g. sodium carbonate or potassium carbonate) or alkali hydrogen carbonates (e.g. sodium hydrogen carbonate or potassium hydrogen carbonate) can be used. As organic base preferably trialkyl amines (e.g. triethylamine) or pyridines (e.g. 4-dimethylaminopyridine (DMAP)) can be used. For example protection of amino compound 18 with ethyl chloroformate in the presence of sodium bicarbonate and DMAP in dichlorometane gives carbamate 19.

The resulting protected structure is coupled with alkynes to form novel imidazo[1,2-a]pyrrolo[3,2-c]pyridines, in one or two-step process, via a palladium catalyzed reaction in a dry inert organic solvent containing a soluble palladium catalyst, in the presence of a proton acceptor, being an aromatic amine, alkylamine or inorganic base, a source of halide ion and at a temperature of about 25°-150° C. The alkynes of the formula $R^xC≡CR^y$ useful in the reaction can be selected from the following classes wherein $R^x$ and $R^y$ can be individually, but not limited to hydrogen, unsubstituted or substituted alkyl or aryl, unsubstituted or substituted alkyl or aryl carboxylates, silyls, aldehydes, alcohols. The organic solvent useful in the process and the palladium catalyst are soluble and compatible and is chemically inert under the reaction conditions. Preferred are DMSO (dimethylsulfoxide) and amide solvents such as DMF (dimethylformamide), DMAC (N,N-dimethylacetamide), and NMP (N-methyl-pyrrolidinone). Most preferred is DMF. Suitable classes of proton acceptors include alkylamines, aromatic amines, heterocyclic amines, inorganic acetates or carbonates, and phosphates. Alkylamines are the preferred proton acceptor in the process of the present invention. Particular alkylamines that may be employed include: DABCO (1,4-diazabicyclo[2.2.2]octane), quinuclidine, butylamine, di-tert-butylamine and triethylamine. Triethylamine is particularly preferred. The proton acceptor is generally employed in excess based on the halogenoimidazopyridines. A useful range is about 2 to 4 fold excess. The palladium catalyst useful in the reaction can be selected from the following classes: Pd alkanoates, Pd acetonates, Pd halides, Pd halide complexes, Pd-benzylidine acetone complexes, as well as triaryl Pd phosphine complexes. Representative examples include, but are not limited to: Pd(II) acetate, Pd(II) acetylacetonate, Pd(0)bis-dibenzylidene acetone ("dba"), Pd(II) bromide, Pd(II) chloride, Pd(II) iodide, Pd(II) sulfate, Pd(II) trifluoroacetate, Pd(II) $Cl_2(CH_3CN)_2$, $Pd_2(dba)_3$, Pd(0) $(PPh_3)_4$, Pd(II) $Cl_2(PPh_3)_2$ and Pd(II) $Cl_2(PhCN)_2$. The palladium catalyst is employed in an amount of about 0.5 to 10 mole percent based on the halogenoimidazopyridines. A source of halide, such as chloride ion, is also preferably used in the present process, in an amount effective to promote the reaction and increase the yield. Organic halide sources, such as tetra(alkyl)ammonium halides, wherein the alkyls can each be about $(C_2-C_{12})$alkyl and wherein halides is F, Cl, Br or I, are preferred, i.e., (n-Bu)$_4$NCl, (n-Bu)$_4$NBr or (n-Bu)$_4$NF. Alkali metal halides such as MX, wherein M is Cu, Li, Na, or K and X is Cl, Br or I, can also be used. In some cases, addition of catalytic amounts of triphenylphosphine (PPh$_3$) was found to improve the yield of product. A dehydrating agent, such as magnesium sulfate or molecular sieves may also be favourably employed in the process of coupling. The reaction is carried out in the temperature range of 25 to 150° C. Generally, the reaction is carried out under a dry, inert atmosphere at atmospheric pressure. It is useful to carry out the reaction under an argon atmosphere. As example carbamate 19 reacts with phenylacetylene in the presence of bis(triphenylphosphine)palladium(II) chloride, triethylamine and copper(I) iodide in dimethylformamide at 60° C. to afford 7-ethoxycarbonyl-2-methyl-8-phenylimidazo[1,2-a]pyrrolo[3,2-c]pyridine 20.

Scheme 8

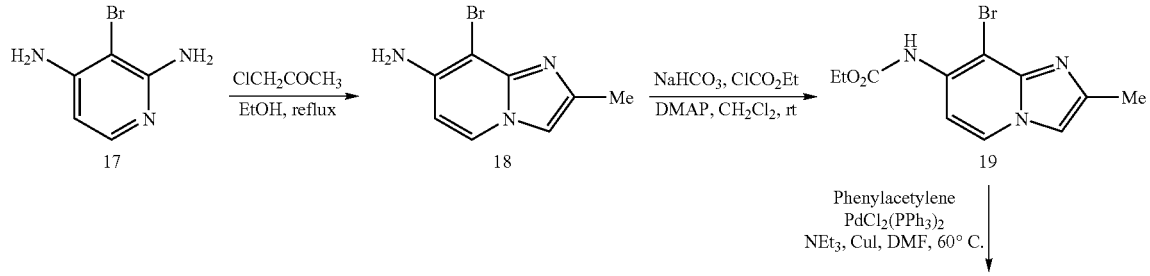

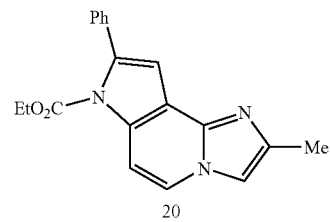

As an other example depicted in scheme 9, carbamate 24 reacts with various alkynes in the presence of bis(triphenylphosphine)palladium(II) chloride, triethylamine and copper(I) iodide in dimethylformamide at room temperature to afford alkyne derivatives 25ac. These compounds react with tetrabutylammonium fluoride in tetrahydrofuran at 50° C. to give 26a,b. The unprotected tricyclic derivatives 27a-c can also be obtained from 25a-c in presence of copper(II) acetate in 1,2-dichloroethane at 65° C.

presence of a proton acceptor, being an aromatic amine, alkylamine or inorganic base and at a temperature of about 25°-150° C. The alkynes of the formula R″C≡CR‴ useful in the reaction can be selected from the following classes wherein R″ and R‴ can be individually, but not limited to hydrogen, unsubstituted or substituted alkyl or aryl, unsubstituted or substituted alkyl or aryl carboxylates, silyls, aldehydes, alcohols. The organic solvent useful in the process and the copper (I) catalyst are soluble and compatible and is chemically inert

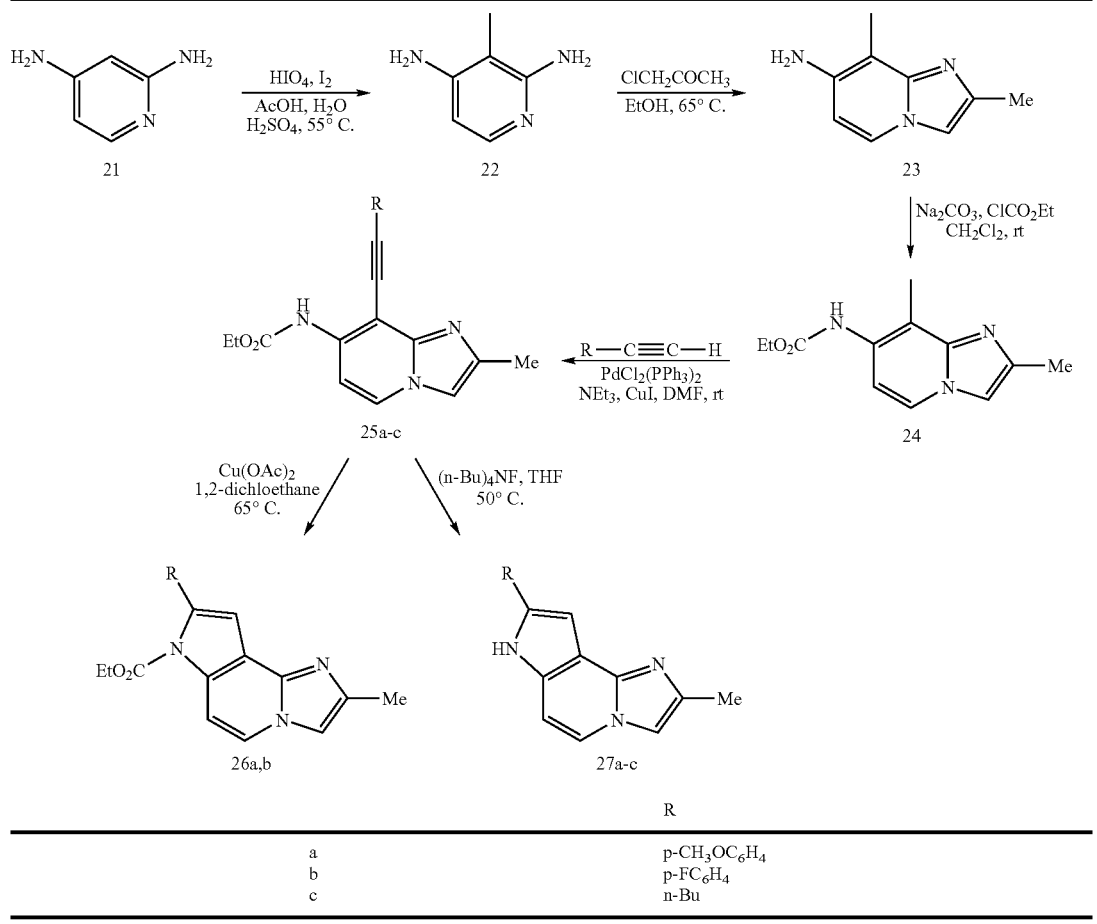

Scheme 9

| | R |
|---|---|
| a | p-CH₃OC₆H₄ |
| b | p-FC₆H₄ |
| c | n-Bu |

In an alternative route depicted in scheme 10, the resulting protected structure is coupled with alkynes to form novel imidazo[1,2-a]pyrrolo[3,2-c]pyridines, in one step procedure, via a copper-catalyzed coupling-cyclization process (Cacchi, S. and al. Org. Lett. 2003, 5, 3843-3846) in a dry inert organic solvent containing a copper(I) catalyst, in the under the reaction conditions. Preferred are toluene, dioxane, DMSO (dimethylsulfoxide) and amide solvents such as DMF (dimethylformamide), DMAC (N,N-dimethylacetamide), and NMP (N-methyl-pyrrolidinone). Most preferred is DMF. Suitable classes of proton acceptors include alkylamines, aromatic amines, heterocyclic amines, inorganic acetates or carbonates, and phosphates. Inorganic phosphates are the preferred proton acceptor in the process of the present invention. Potassium phosphate is particularly preferred. The proton acceptor is generally employed in excess based on the halogenoimidazopyridines. A useful range is about 2 to 4 fold excess. The copper(I) catalyst of the formula [CuL$_n$]X, where Cu(I) is tetracoordinated, useful in the reaction can be selected from the following classes wherein L is a neutral mono or polydentate ligand choose individually but not limited to acetonitrile, triphenylphosphine, 1,10-phenantroline, pyridine, ethylenediamine, 2,2'-bipyridine, 1,2-bis(diphenylphosphino)ethane, tri(o-tolyl)phosphine or an other appropriate ligand and wherein X is a monovalent anion such as F, Cl, Br, I, NO$_3$. Preferentially, L is triphenylphosphine and 1,10-phenantroline and X is a nitrate. [Cu(phen)(PPh$_3$)$_2$] NO$_3$ is particularly preferred. The copper catalyst is employed in an amount of about 0.5 to 15 mole percent based on the halogenoimidazopyridines. The reaction is carried out in the temperature range of 25 to 150° C. Generally, the reaction is carried out under a dry, inert atmosphere at atmospheric pressure. It is useful to carry out the reaction under an argon atmosphere. As Example amide derivative 28 afford in presence of phenylacetylene, 1,10-phenanthrolinebis(triphenylphosphine)copper(I) nitrate and potassium phosphate in dimethylformamide (DMF) at 115° C. the 2-methyl-8-phenylimidazo[1,2-a]pyrrolo[3,2-c]pyridine 29.

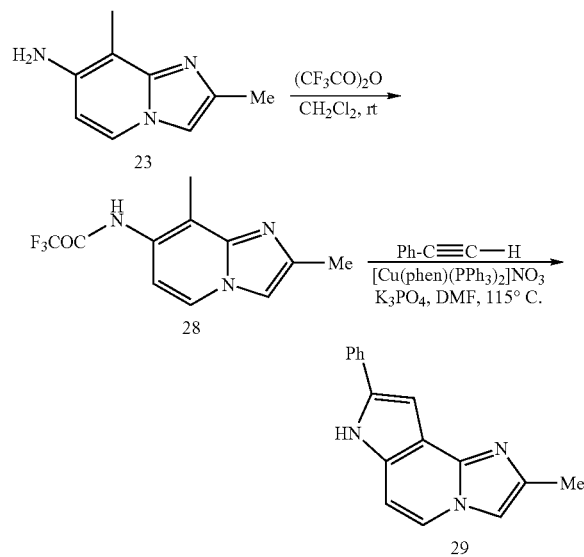

Substituent in R$^6$ position can be also introduced in two steps from 7-amino-8-halogenoimidazo[1,2-a]pyridines developed above according to the Heck procedure (Humphrey, G. R. and al. Chem. Rev. 2006, 106, 2875-2911) as depicted in scheme 11.

Briefly, this reaction involve formation of enamines followed by an intramolecular palladium catalysis cyclization. Enamines can be obtained from amino derivatives by condensation of various aliphatic ketones in appropriate solvent or by reaction with alkenylhalides (or triflate) in presence of sodium hydride, with or without tetrabutylammonium bromide, in appropriate dry aprotic solvent and at a temperature of about 25 to 100° C. The alkenylhalides of the formula R''''—CH═CH—CH$_2$X useful in the reaction can be selected from the following classes wherein R'''' can be, but not limited to hydrogen, unsubstituted or substituted alkyl and wherein X is an halogen such as Cl, Br and I. The dry organic solvent useful in the process is chemically inert under the reaction conditions, preferably halogenated aliphatic hydrocarbons (e.g. dichloromethane, dichloroethane or chloroform) or etheral solvents (i.e. diethylether, tetrahydrofuran or dimethoxyethane) can be used. The resulting enamine structure afford novel imidazo[1,2-a]pyrrolo[3,2-c]pyridines via a palladium catalyzed reaction in a dry inert organic solvent containing a soluble palladium catalyst, in the presence of a proton acceptor, being an aromatic amine, alkylamine or inorganic base, a source of halide ion and at a temperature of about 25°-150° C. The organic solvent useful in the process and the palladium catalyst are soluble and compatible and is chemically inert under the reaction conditions. Preferred are DMSO (dimethylsulfoxide) and amide solvents such as DMF (dimethylformamide), DMAC (N,N-dimethylacetamide), and NMP (N-methyl-pyrrolidinone). Most preferred is DMF. Suitable classes of proton acceptors include alkylamines, aromatic amines, heterocyclic amines, inorganic acetates or carbonates, and phosphates. Alkylamines are the preferred proton acceptor in the process of the present invention. Particular alkylamines that may be employed include: DABCO (1,4-diazabicyclo[2.2.2]octane), quinuclidine, butylamine, di-tert-butylamine and triethylamine. Triethylamine is particularly preferred. The proton acceptor is generally employed in excess based on the halogenoimidazopyridines. A useful range is about 2 to 4 fold excess. The palladium catalyst useful in the reaction can be selected from the following classes: Pd alkanoates, Pd acetonates, Pd halides, Pd halide complexes, Pd-benzylidine acetone complexes, as well as triaryl Pd phosphine complexes. Representative examples include, but are not limited to: Pd(II) acetate, Pd(II) acetylacetonate, Pd(0)bis-dibenzylidene acetone ("dba"), Pd(II) bromide, Pd(II) chloride, Pd(II) iodide, Pd(II) sulfate, Pd(II) trifluoroacetate, Pd(II) Cl$_2$(CH$_3$CN)$_2$, Pd$_2$ (dba)$_3$, Pd(0) (PPh$_3$)$_4$, Pd(II) Cl$_2$(PPh$_3$)$_2$ and Pd(II) Cl$_2$(PhCN)$_2$. The palladium catalyst is employed in an amount of about 0.5 to 15 mole percent based on the halogenoimidazopyridines. A source of halide, such as chloride ion, is also preferably used in the present process, in an amount effective to promote the reaction and increase the yield. Organic halide sources, such as tetra(alkyl)ammonium halides, wherein the alkyls can each be about (C$_2$-C$_{12}$)alkyl, wherein halides is F, Cl, Br or I are preferred, i.e., (n-Bu)$_4$NCl, (n-Bu)$_4$NBr or (n-Bu)$_4$NF. Alkali metal halides such as MX, wherein M is Cu, Li, Na, or K and X is Cl, Br or I, can also be used. The reaction is carried out in the temperature range of 25 to 150° C. Generally, the reaction is carried out under a dry, inert atmosphere at atmospheric pressure. It is useful to carry out the reaction under an argon atmosphere. As an example, aminoallyl derivative 30 obtained from 7-amino-8-iodoimidazo[1,2-a]pyridine 23 afford in presence of palladium(II) acetate, triethylamine and tetrabutylammonium bromide in dimethylformamide at room temperature the 2,9-dimethylimidazo[1,2-a]pyrrolo[3,2-c]pyridine 31.

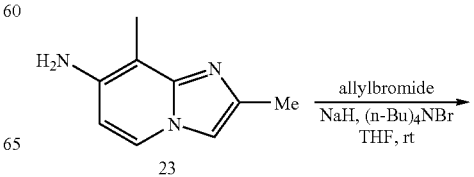

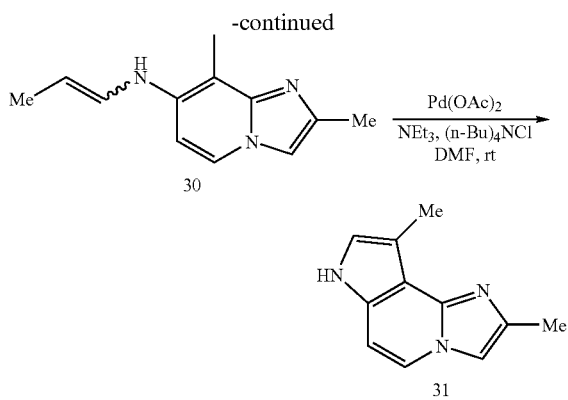

In antiviral assays for detection of anti-BVDV activity, we found that the newly synthesized imidazo[1,2-a]pyrrolo[3,2-c]pyridines were active towards BVDV in the assays described herein. As an example, compound 15 showed a selectivity index of over 200 ($EC_{50}$=0.5 µg/mL and $CC_{50}$>100 µg/mL. Some results are shown in Table 1, which indicate the 50% inhibitory concentrations for the inhibition of viral replication ($EC_{50}$) and host growth ($CC_{50}$), as well as the selectivity index (SI=$CC_{50}/EC_{50}$).

The compounds of the invention can be employed for the treatment or prophylaxis of viral infections, more particularly Flaviviral infections, in particular of BVDV or HCV. When using one or more derivatives of the formula I, II or III as defined herein:
- the active ingredients of the compound(s) may be administered to the mammal (including a human) to be treated by any means well known in the art, i.e. orally, intranasally, subcutaneously, intramuscularly, intradermally, intravenously, intra-arterially, parenterally or by catheterization.
- the therapeutically effective amount of the preparation of the compound(s), especially for the treatment of viral infections in humans and other mammals, preferably is a flaviviral or herpesviridae enzyme inhibiting amount. More preferably, it is a flaviviral replication inhibiting amount or a flaviviral enzyme inhibiting amount of the derivative(s) of formula (I) as defined herein corresponds to an amount which ensures a plasma level of between 1 µg/ml and 100 mg/ml, optionally of 10 mg/ml. Depending upon the pathologic condition to be treated and the patient's condition, the said effective amount may be divided into several sub-units per day or may be administered at more than one day intervals.

The present invention further relates to a method for preventing or treating a viral infections in a subject or patient by administering to the patient in need thereof a therapeutically effective amount of the compounds of the present invention. The therapeutically effective amount of the compound(s), especially for the treatment of viral infections in humans and other mammals, preferably is a flaviviral enzyme inhibiting amount. More preferably, it is a flaviviral replication inhibiting amount or a flaviviral enzyme inhibiting amount of the derivative(s) of formula I, II or III as defined herein. Depending upon the pathologic condition to be treated and the patient's condition, the said effective amount may be divided into several sub-units per day or may be administered at more than one day intervals.

The present invention also relates to a combination of different antiviral drugs of the invention or to a combination of the antiviral drugs of the invention with other drugs that exhibit anti-BVDV or anti-HCV activity.

The invention also relates to a pharmaceutical composition or combined preparation of antiviral drugs and containing:
Either:
A)
(a) a combination of two or more of the imidazo[1,2-a]pyrrolo[3,2-c]pyridine derivatives of the present invention, and
(b) optionally one or more pharmaceutical excipients or pharmaceutically acceptable carriers,
for simultaneous, separate or sequential use in the treatment or prevention of a viral infection
or
B)
(c) one or more anti-viral agents, and
(d) at least one of the imidazo[1,2-a]pyrrolo[3,2-c]pyridine derivatives of the present invention, and
(e) optionally one or more pharmaceutical excipients or pharmaceutically acceptable carriers,
for simultaneous, separate or sequential use in the treatment or prevention of a viral infection.

Suitable anti-viral agents for inclusion into the antiviral compositions or combined preparations of this invention include for instance, inhibitors of BVDV or HCV replication respectively, such as interferon-alfa (either pegylated or not), ribavirin and other selective inhibitors of the replication of HCV, such as a compound faling within the scope of disclosure EP1162196, WO 03/010141, WO 03/007945 and WO 03/010140, a compound falling within the scope of disclosure WO 00/204425, and other patents or patent applications within their patent families or all the foregoing filings and/or an inhibitor of flaviviral protease and/or one or more additional flavivirus polymerase inhibitors.

The pharmaceutical composition or combined preparation with activity against viral infection according to this invention may contain the imidazo[1,2-a]pyrrolo[3,2-c]pyridine derivatives of the present invention over a broad content range depending on the contemplated use and the expected effect of the preparation. Generally, the content of the imidazo[1,2-a]pyrrolo[3,2-c]pyridine derivatives of the present invention of the combined preparation is within the range of 0.1 to 99.9% by weight, preferably from 1 to 99% by weight, more preferably from 5 to 95% by weight.

When using a pharmaceutical composition of combined preparation:
- the active ingredients may be administered to the mammal (including a human) to be treated by any means well known in the art, i.e. orally, intranasally, subcutaneously, intramuscularly, intradermally, intravenously, intra-arterially, parenterally or by catheterization.
- the therapeutically effective amount of each of the active agents, especially for the treatment of viral infections in humans and other mammals, particularly is a flaviviral enzyme inhibiting amount.

When applying a combined preparation, the active ingredients may be administered simultaneously but it is also beneficial to administer them separately or sequentially, for to instance within a relatively short period of time (e.g. within about 24 hours) in order to achieve their functional fusion in the body to be treated.

The invention also relates to the compounds of the formulas described herein being used for inhibition of the proliferation of other viruses than BVDV or HCV, particularly for the inhibition of other members of the family of the Flaviviridae, including but not limited to the Yellow fever virus, the Dengue fever virus, West Nile virus, Japanese encephalitis virus, hepatitis G virus, classical swine fever virus, border disease virus but also for the inhibition of other viruses including HIV and other retroviruses.

The present invention further provides veterinary compositions comprising at least one active ingredient as above defined together with a veterinary carrier therefor, for example in the treatment of BVDV. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

More generally, the invention relates to the compounds of formulas I, II and III being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

The compounds of the invention optionally are bound covalently to an insoluble matrix and used for affinity chromatography separations, depending on the nature of the groups of the compounds, for example compounds with pendant aryl are useful in hydrophobic affinity separations.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formula I, II and III are able to form. Therefore, the compounds of this invention optionally comprise salts of the compounds herein, especially pharmaceutically acceptable non-toxic salts containing, for example, $Na^+$, $Li^+$, $K^+$, $Ca^{2+}$ and $Mg^{2+}$. Such salts may include those derived by combination of appropriate cations such as alkali and alkaline earth metal ions or ammonium and quaternary amine ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formula I, II and III as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates. Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and sterochemical forms, which the compounds of formula I, II and III may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formula I, II and III may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question. Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of formula I, II and III may easily be determined by those skilled in the art while using well-known methods such as, for example, X-ray diffraction.

The compounds of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty, acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphosphatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw", 2 d ed. (Hanser Verlag, Vienna, 1981) and "Encyclopaedia of Surfactants" (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

The compounds of formula I, II and III, can be prepared while using a series of chemical reactions well known to those skilled in the art, altogether making up the process for preparing said compounds and exemplified further. The processes described further are only meant as examples and by no means are meant to limit the scope of the present invention.

EXAMPLES

The following examples illustrate the present invention without being limited thereto. Part A represent the preparation of the imidazo[1,2-a]pyrrolo[3,2-c]pyridines whereas Part B represents the pharmacological examples. Analoguous compounds of the ones specifically mentioned herein are synthesised in the same fashion as in the foregoing schemes and following examples by varying the starting materials, intermediates, solvents and conditions as is known by those skilled in the art.

TABLE 1

Examples of the compounds of the invention are

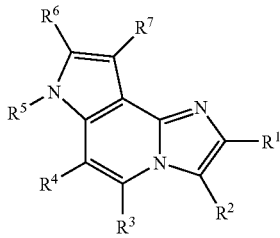

| Compound Code | $R^1$ | $R^2$ | $R^3$ | $R^4$ | $R^5$ | $R^6$ | $R^7$ |
|---|---|---|---|---|---|---|---|
| 7i | Br | H | H | H | H | $CO_2Et$ | H |
| 7a | H | H | H | H | H | $CO_2Et$ | H |
| 7j | H | Br | H | H | H | $CO_2Et$ | H |
| 7b | Me | H | H | H | H | $CO_2Et$ | H |
| 7c | Ph | H | H | H | H | $CO_2Et$ | H |
| 7d | m-$CH_3OC_6H_4$ | H | H | H | H | $CO_2Et$ | H |
| 7h | $CH(OEt)_2$ | H | H | H | H | $CO_2Et$ | H |
| 7k | Me | Br | H | H | H | $CO_2Et$ | H |
| 7l | Me | $NO_2$ | H | H | H | $CO_2Et$ | H |
| 7e | $CF_3$ | H | H | H | H | $CO_2Et$ | H |
| 7f | i-Pr | H | H | H | H | $CO_2Et$ | H |
| 7g | t-Bu | H | H | H | H | $CO_2Et$ | H |
| 8 | CHO | H | H | H | H | $CO_2Et$ | H |
| 9 | $CH_2N(CH_3)_2$ | H | H | H | H | $CO_2Et$ | H |
| 10 | Br | H | H | H | H | $CH_2OH$ | H |
| 11 | $CH_2OH$ | H | H | H | H | $CO_2Et$ | H |
| 12 | $CH_2Cl$ | H | H | H | H | $CO_2Et$ | H |
| 13 | Me | H | H | H | Me | $CO_2Et$ | H |
| 14 | Me | H | H | H | Me | $CO_2Me$ | H |
| 15 | Me | H | H | H | H | $CO_2H$ | H |
| 16a | Me | H | H | H | H | $CO_2Me$ | H |
| 16b | Me | H | H | H | H | $CO_2Bu$ | H |
| 20 | Me | H | H | H | $CO_2Et$ | Ph | H |
| 26a | Me | H | H | H | $CO_2Et$ | p-$CH_3OC_6H_4$ | H |
| 26b | Me | H | H | H | $CO_2Et$ | p-$FC_6H_4$ | H |
| 27a | Me | H | H | H | H | p-$CH_3OC_6H_4$ | H |
| 27b | Me | H | H | H | H | p-$FC_6H_4$ | H |
| 26c | Me | H | H | H | H | n-Bu | H |
| 29 | Me | H | H | H | H | Ph | H |
| 31 | Me | H | H | H | H | H | Me |

Abbreviations:
"Me" is $CH_3$;
"Ph" is phenyl;
"Et" is —$CH_2CH_3$;
"Bu" is butyl.

Part A: Preparation of the Compounds of the Invention

Procedures and Instrumentation used for the preparation of all the exemplified compounds as described herein: All column chromatography was performed with Merck neutral Aluminum oxide 90 standardized (63-200 μm) unless otherwise specified. All thin-layer chromatography was performed on Merck neutral Aluminum oxide $60F_{254}$ plates. The plates were visualized with UV light (254 nm). Melting points were determined on an electrothermal IA9300 (capillary) and are not corrected. NMR (400 or 200 MHz for $^1H$ or 100 or 50 MHz for $^{13}C$) were recorded on a Bruker Avance 400 or Bruker AM 200 instruments using $CDCl_3$, $CD_3OD$, acetone-$d_6$ and DMSO-$d_6$ as solvent. Infrared spectra were recorded on a FTIR Nicolet impact 410. Mass spectral analyses were performed on a Hewlett-Packard 5985B or 5989A instrument. All air-sensitive reactions were run under argon atmosphere. All solvents were dried using common techniques.

Example 1

General Procedure for Synthesis of ethyl imidazo[1,2-a]pyridine-8-carboxylates 2a-g To a solution of ethyl 2-aminopyridine-3-carboxylate (1) (0.50 g, 3.01 mmol-Zhou, Z. L. and al. Bioorg. Med. Chem. 2001, 9, 2061-2071) in appropriated solvent (20 mL) was added an halogenated ketone or aldehyde. The mixture was refluxed for 6-90 h. After cooling, the solvent was removed under reduced pressure and an aqueous saturated $NaHCO_3$ solution was added (40 mL). The organic layers were extracted with $CH_2Cl_2$, dried ($Na_2SO_4$), filtered and evaporated under reduced pressure. The residue was purified by column chromatography.

Example 2

Ethyl (imidazo[1,2-a]pyridin-8-yl)carboxylate (2a)

From chloracetaldehyde (50% in water, 13:6 mmol) using ethanol as solvent, reaction time 9 h, chromatography using $CH_2Cl_2$ as eluent (yield: 86%); mp 48-50° C. (in U.S. Pat. No. 5,294,612: 59-61° C.); IR (KBr) 1720, 1365, 1250, 780 cm$^{-1}$; $^1H$ NMR (400 MHz, $CDCl_3$) δ 1.47 (t, 1H, J=7 Hz), 4.55 (q, 2H, J=7 Hz), 6.95 (t, 1H, J=6.5 Hz), 7.78 (s, 1H), 7.83 (s, 1H), 8.03 (d, 1H, J=6.5 Hz), 8.44 (d, 1H, J=6.5 Hz); $^{13}C$ NMR (100 MHz, $CDCl_3$) δ 14.3, 61.6, 111.2, 113.0, 120.1, 129.0, 129.7, 134.5, 142.5, 164.0.

Example 3

Ethyl (2-methylimidazo[1,2-a]pyridin-8-yl)carboxylate (2b)

From chloracetone (21.1 mmol) using ethanol as solvent, chromatography using AcOEt/cyclohexane (6/4, v/v) as eluent to afford in order of elution: starting material (0.84 mmol); compound 2b (yield: 50%); mp 62-64° C.; IR (KBr) 1720, 1272 cm$^{-1}$; $^1H$ NMR (200 MHz, $CDCl_3$) δ 1.33 (t, 1H, J=7 Hz), 2.40 (s, 3H), 4.37 (q, 2H, J=7 Hz), 6.67 (t, 1H, J=7 Hz), 7.31 (s, 1H), 7.75 (d, 1H, J=7 Hz), 8.13 (d, 1H, J=7 Hz); $^{13}C$ NMR (100 MHz, $CDCl_3$) δ 13.7, 14.22, 61.3, 110.2, 110.4, 118.9, 128.0, 129.0, 142.2, 144.6, 164.3; MS m/z 204 (M$^+$, 11), 159 (8), 132 (100), 104 (13), 77 (9).

Example 4

Ethyl (2-phenylimidazo[1,2-a]pyridin-8-yl)carboxylate (2c)

From chloroacetophenone (5.98 mmol) using ethanol as solvent, reaction time 72 h, chromatography using AcOEt/cyclohexane (6/4, v/v) as eluent to give in order of elution: compound 2c (yield: 56%) as an oil; IR ($CCl_4$) 1712, 1288 $cm^{-1}$; $^1H$ NMR (400 MHz, $CDCl_3$) δ 1.36 (t, 3H, J=7 Hz), 4.39 (q, 2H, J=7 Hz), 6.63 (t, 1H, J=7 Hz), 7.20 (t, 1H, J=7.5 Hz), 7.28 (t, 2H, J=7.5 Hz), 7.75 (s; 1H), 7.77 (d, 1H, J=7 Hz), 7.88 (d, 2H, J=7.5 Hz), 8.12 (d, 1H, J=7 Hz); $^{13}C$ NMR (100 MHz, $CDCl_3$) δ 14.3, 61.2, 108.8, 111.2, 119.6, 126.3, 128.2, 128.8, 129.0, 129.5, 133.3, 142.9, 146.6, 164.5; MS m/z 266 ($M^+$, 18), 194 (100), 102 (19). Starting material (0.39 mmol).

Example 5

Ethyl (2-(3-methoxyphenyl)imidazo[1,2-a]pyridin-8-yl)carboxylate (2d)

From 2-bromo-3'-methoxyacetophenone (4.52 mmol) using butanol as solvent, reaction time 6 h, chromatography using $CH_2Cl_2$ as eluent (yield: 43%) as an oil; IR ($CCl_4$) 1711, 1549, 1255 $cm^{-1}$; $^1H$ NMR (400 MHz, $CDCl_3$) δ 1.47 (t, 3H, J=7 Hz), 3.86 (s, 3H), 4.49 (q, 2H, J=7 Hz), 6.77 (t, 1H, J=7 Hz), 6.86 (dd, 1H, J=2.5, 8 Hz), 7.29 (t, 1H, J=8 Hz), 7.52 (d, 1H, J=8 Hz), 7.61 (d, 1H, J=2.5 Hz), 7.85 (s, 1H), 7.88 (d, 1H, J=7 Hz), 8.22 (d, 1H, J=7 Hz); $^{13}C$ NMR (100 MHz, $CDCl_3$) δ 14.3, 55.3, 61.5, 108.9, 111.2, 111.5, 114.3, 118.2, 119.9, 128.9, 129.4, 129.6, 134.8, 142.9, 146.7, 160.0, 164.6; MS m/z 296 ($M^+$, 28), 224 (100), 193 (18), 89 (13).

Example 6

Ethyl (2-trifluoromethylimidazo[1,2-a]pyridin-8-yl)carboxylate (2e)

From 3-bromo-1,1,1-trifluoroacetone (9.03 mmol) using ethanol as solvent, reaction time 90 h, chromatography using $CH_2Cl_2$ as eluent to give in order of elution: compound 2e (yield: 67%); mp 108-110° C.; IR (KBr) 1725, 1283, 1206, 1166 $cm^{-1}$; $^1H$ NMR (400 MHz, $CDCl_3$) δ 1.42 (t, 3H, J=7 Hz), 4.46 (q, 2H, J=7 Hz), 7.00 (t, 1H, J=7 Hz), 8.04 (m, 2H), 8.46 (d, 1H, J=7 Hz); $^{13}C$ NMR (100 MHz, $CDCl_3$) δ 14.2, 61.8, 112.6, 112.9, 121.1, 121.4 (d, $^1J_{F-C}$=267 Hz), 130.4, 130.8, 136.7 (q, $^2J_{F-C}$=39 Hz), 142.7, 163.5; MS m/z 258 ($M^+$, 17), 213 (15), 186 (100), 166 (14). Starting material (0.84 mmol).

Example 7

Ethyl (2-isopropylimidazo[1,2-a]pyridin-8-yl)carboxylate (2f)

From 1-bromo-3-methylbutanone (9.03 mmol-obtained from bromination of 3-methylbutanone in methanol according to the literature method: Gaudry, M. and al. *Org. Synth.* 1976, 55, 24-27. using ethanol as solvent, reaction time 40 h, chromatography using AcOEt/cyclohexane (8/2, v/v) as eluent to give in order of elution: compound 2f (yield: 70%) as an oil; IR ($CCl_4$) 1712, 1283 $cm^{-1}$; $^1H$ NMR (400 MHz, $CDCl_3$) δ 1.27 (d, 6H, J=7 Hz), 1.33 (t, 3H, J=7 Hz), 3.12 (sept, 1H, J=7 Hz), 4.36 (q, 2H, J=7 Hz), 6.66 (t, 1H, J=7 Hz), 7.32 (s, 1H), 7.75 (d, 1H, J=7 Hz), 8.18 (d, 1H, J=7 Hz); $^{13}C$ NMR (100 MHz, $CDCl_3$) δ 14.2, 22.4, 28.6, 61.2, 108.0, 110.3, 119.1, 128.0, 129.3, 142.1, 155.6, 171.0; MS m/z 232 ($M^+$, 26), 217 (18), 171 (34), 160 (100). Starting material (0.66 mmol).

Example 8

Ethyl (2-tert-butylimidazo[1,2-a]pyridin-8-yl)carboxylate (2g)

From 1-bromopinacolone (6.02 mmol) using ethanol as solvent, reaction time 72 h, chromatography using $CH_2Cl_2$ as eluent (yield: 73%); mp 72-74° C.; IR (KBr) 1690, 1287 $cm^{-1}$; $^1H$ NMR (400 MHz, $CDCl_3$) δ 1.41 (m, 12H), 4.41 (q, 2H, J=7 Hz), 6.71 (t, 1H, J=7 Hz), 7.38 (s, 1H), 7.82 (d, 1H, J=7 Hz), 8.21 (d, 1H, J=7 Hz); $^{13}C$ NMR (100 MHz, $CDCl_3$) δ 30.2, 32.5, 62.2, 107.4, 110.2, 119.4, 128.0, 129.3, 142.1, 158.5, 164.1; MS m/z 246 ($M^+$, 57), 231 (55), 185 (86), 174 (100). Starting material (0.66 mmol).

Example 9

Ethyl (2-dichloromethylimidazo[1,2-a]pyridin-8-yl)carboxylate (2h)

To a stirred solution of ethyl 2-aminopyridine-3-carboxylate (1) (4.28 g, 25.8 mmol, Zhou, Z. L and al. Bioorg. Med. Chem. 2001, 9, 2061-2071) in 1,2-dimethoxyethane (DME) (100 mL) was added dropwise a solution of 1,1,3-trichloracetone (8.32 g, 51.5 mmol) in DME (15 mL). The mixture was stirred at room temperature for 76 h. The resulting precipitate was collected by filtration and washed with DME (2×15 mL). The solid was poured into dry ethanol (100 mL) and heated under reflux for 18 h. The cooled solution was evaporated and an aqueous saturated $NaHCO_3$ solution (40 mL) was added. The mixture was extracted with $CH_2Cl_2$ and the organic layers were dried ($MgSO_4$), filtered and evaporated to dryness. The residue was purified by chromatography using $CH_2Cl_2$ as eluent to give in order of elution: dichloro compound 2h (4.95 g, 70%); mp 108-110° C.; IR (KBr) 1719, 1279 $cm^{-1}$; $^1H$ NMR (200 MHz, $CDCl_3$) δ 1.44 (t, 3H, J=7 Hz), 4.51 (q, 2H, J=7 Hz), 6.99 (t, 1H, J=7 Hz), 7.12 (s, 1H), 8.03 (m, 2H), 8.39 (d, 1H, J=7 Hz); $^{13}C$ NMR (100 MHz, $CDCl_3$) δ 14.3, 62.0, 65.3, 112.0, 112.7, 120.3, 130.3, 130.7, 141.6, 146.3, 163.5. MS m/z 276 ($M^++4$, 2), 274 ($M^++2$, 13), 272 ($M^+$, 17), 237 (29), 202 (63), 200 (100), 166 (27), 129 (47).

Example 10

Ethyl (2-diethoxymethylimidazo[1,2-a]pyridin-8-yl)carboxylate (2i)

To a solution of dichloro compound 2h (1.00 g, 3.66 mmol) in dry ethanol (100 mL), under argon, was added 4-dimethylaminopyridine (DMAP) (0.90 g, 7.38 mmol). The solution was stirred under reflux for 20 h. After cooling to room temperature, the solution was concentrated under vacuo. The resulting precipitate was suspended in ethyl acetate (30 mL), filtered and washed with AcOEt (3×10 mL). The filtrate was evaporated to dryness. The crude product was chromatographed using AcOEt/cyclohexane (8/2, v/v) as eluent to afford compound 2i (1.04 g, 97%). Ketal compound 2i (0.30 g, 4%); mp 98-100° C.; IR (KBr) 1716, 1267, 1166 $cm^{-1}$; $^1H$ NMR (400 MHz, $CDCl_3$) δ 1.24 (t, 6H, J=7 Hz), 1.41 (t, 3H, J=7 Hz), 3.68 (m, 4H), 4.46 (q, 2H, J=7 Hz), 5.81 (s, 1H), 6.85 (t, 1H, J=7 Hz), 7.78 (s, 1H), 7.90 (d, 1H, J=7 Hz), 8.32 (d, 1H, J=7 Hz); $^{13}$C NMR (100 MHz, CDCl$_3$) δ 14.3, 15.3, 61.6, 62.3, 99.0, 111.0, 111.5, 120.2, 128.9, 129.8, 142.0, 146.3, 164.2. MS m/z 293 (M$^+$+1, 1), 248 (22), 219 (100), 191 (17), 173 (52), 146 (18) 117 (13).

Example 11

Reduction of Ester Compounds 2a-g, i

A solution of esters 2a-g, i (1.32 mmol) in dry THF (10 mL) was added, under argon, to a cold (0° C.) solution of LAH (0.20 g, 5.26 mmol) in dry THF (20 mL). After stirring for 3.5 h, the excess of LAH was decomposed with 3% aqueous NaOH solution. The residue was removed by filtration and washed with hot THF (10 mL) then with CHCl$_3$ (10 mL). The organic layers were dried (MgSO$_4$), filtered and evaporated under reduced pressure. Purification of the crude product by chromatography using CH$_2$Cl$_2$/EtOH (97/3, v/v) as eluent afforded alcohols 3a-g, i.

Example 12

8-Hydroxymethylimidazo[1,2-a]pyridine (3a)

From 2a (yield: 82%); mp 177-479° C.; IR (KBr) 1505, 1300, 1140, 1015, 780, 735 cm$^{-1}$; $^1$H NMR (400 MHz, CDCl$_3$) δ 4.99 (s, 2H), 5.65 (s, 1H), 6.78 (t, 1H, J=6.5 Hz), 7.17 (d, 1H, J=6.5 Hz), 7.27 (s, 1H), 7.59 (s, 1H), 8.08 (d, 1H, J=6.5 Hz); $^{13}$C NMR (100 MHz, CDCl$_3$) δ 58.5, 112.5, 112.7, 121.6, 125.0, 130.0, 132.7, 144.4.

Example 13

8-Hydroxymethyl-2-methylimidazo[1,2-a]pyridine (3b)

From 2b (yield: 42%) as an oil; IR (CCl$_4$) 2960, 1499, 1366, 1324 cm$^{-1}$; $^1$H NMR (400 MHz, CDCl$_3$) δ 2.36 (s, 3H), 4.96 (s, 2H), 6.64 (t, 1H, J=7 Hz), 7.11 (d, 1H, J=7 Hz), 7.25 (s, 1H), 7.88 (d, 1H, J=7 Hz); $^{13}$C NMR (100 MHz, CDCl$_3$) δ 14.0, 60.8, 109.7, 111.9, 121.5, 124.1, 129.2, 142.2, 143.6; MS m/z 162 (M$^+$, 36), 161 (100), 133 (55), 132 (46), 78 (31), 51 (16).

Example 14

8-Hydroxymethyl-2-phenylimidazo[1,2-a]pyridine (3c)

From 2c (yield: 92%); mp 85-87° C.; IR (KBr) 2926, 1731, 1605, 1481, 1371 cm$^{-1}$; $^1$H NMR (400 MHz, CDCl$_3$) δ 4.95 (s, 2H), 6.71 (t, 1H, J=7 Hz), 7.05 (d, 1H, J=7 Hz), 7.32 (t, 1H, J=7.5 Hz), 7.42 (t, 2H, J=7.5 Hz), 7.81 (s, 1H), 7.92 (d, 2H, J=7.5 Hz), 8.00 (d, 1H, J=7 Hz); $^{13}$C NMR (100 MHz, CDCl$_3$) δ 62.4, 108.2, 112.5, 121.5, 124.6, 126.1, 128.1, 128.6, 129.6, 133.3, 144.6, 145.0; MS m/z 224 (M$^+$, 52), 223 (100), 195 (50), 91 (26), 78 (30), 51 (28).

Example 15

8-Hydroxymethyl-2-(3-methoxyphenyl)imidazo[1,2-a]pyridine (3d)

From 2d (yield: 83%) as an oil; IR (CCl$_4$) 2956, 1550, 1253 cm$^{-1}$; $^1$H NMR (400 MHz, CDCl$_3$) δ 3.89 (s, 3H), 5.05 (s, 2H), 6.74 (t, 1H, J=7 Hz), 6.89 (dd, 1H, J=2.5, 8 Hz), 7.06 (d, 1H, J=7 Hz), 7.34 (t, 1H, J=8 Hz), 7.51 (d, 1H, J=8 Hz), 7.54 (d, 1H, J=2.5 Hz), 7.83 (s, 1H), 8.03 (d, 1H, J=7 Hz); $^{13}$C NMR (100 MHz, CDCl$_3$) δ 55.4, 62.6, 108.4, 111.4, 112.4, 113.9, 118.6, 121.4, 124.6, 129.7, 129.8, 134.9, 144.6, 144.9, 160.0; MS m/z 254 (M$^+$, 58), 253 (100), 238 (12), 225 (22), 210 (16).

Example 16

8-Hydroxymethyl-2-trifluoromethylimidazo[1,2-a]pyridine (3e)

From 2e (yield: 54%); mp 118-120° C.; IR (KBr) 3400-3100, 1225, 1163 cm$^{-1}$; $^1$H NMR (400 MHz, CDCl$_3$) δ 5.06 (s, 2H), 6.95 (t, 1H, J=7 Hz), 7.31 (d, 1H, J=7 Hz), 7.92 (s, 1H), 8.11 (d, 1H, J=7 Hz); $^{13}$C NMR (100 MHz, CDCl$_3$) δ 61.7, 111.9, 114.0, 121.5 (d, $^1J_{F-C}$=267 Hz), 123.3, 125.2, 131.0, 135.4 (q, $^2J_{F-C}$=39 Hz), 144.4; MS m/z 216 (M$^+$, 50), 215 (100), 195 (25), 187 (20), 167 (29).

Example 17

8-Hydroxymethyl-2-isopropylimidazo[1,2-a]pyridine (3f)

From 2f (yield: 47%); mp 97-99° C.; IR (KBr) 3250-3000, 2960, 1498, 1307 cm$^{-1}$; $^1$H NMR (400 MHz, CDCl$_3$) δ 1.30 (d, 6H, J=7 Hz), 3.06 (sept, 1H, J=7 Hz), 4.99 (s, 2H), 6.65 (t, 1H, J=7 Hz), 7.07 (d, 1H, J=7 Hz), 7.27 (s, 1H), 7.92 (d, 1H, J=7 Hz); $^{13}$C NMR (100 MHz, CDCl$_3$) δ 22.5, 28.3, 62.6, 107.5, 111.8, 121.5, 124.4, 129.3, 143.7, 153.3; MS m/z 190 (M$^+$, 43), 189 (100), 161 (25), 157 (23), 78 (15).

Example 18

2-tert-Butyl-8-hydroxymethylimidazo[1,2-a]pyridine (3g)

From 2g (yield: 52%) as an oil; IR (CCl$_4$) 2962, 1498 cm$^{-1}$; $^1$H NMR (400 MHz, CDCl$_3$) δ 1.09 (s, 9H), 4.72 (s, 2H), 5.01 (s, 1H), 6.39 (t, 1H, J=7 Hz), 6.73 (d, 1H, J=7 Hz), 7.03 (s, 1H), 7.67 (d, 1H, J=7 Hz); $^{13}$C NMR (100 MHz, CDCl$_3$) δ 30.1, 32.2, 62.4, 106.8, 111.6, 124.4, 129.1, 143.9, 156.4; MS m/z 204 (M$^+$, 53), 203 (100), 175 (24), 171 (55).

Example 19

2-Diethoxymethyl-8-hydroxymethylimidazo[1,2-a]pyridine (3i)

From 2i (yield: 60%); mp 87-89° C.; IR (KBr) 2977, 1148 cm$^{-1}$; $^1$H NMR (400 MHz, CDCl$_3$) δ 1.25 (t, 6H, J=7 Hz), 3.68 (m, 4H), 4.52 (brs, 1H), 5.02 (s, 2H), 5.71 (s, 1H), 6.75 (t, 1H, J=7 Hz), 7.12 (d, 1H, J=7 Hz), 7.65 (s, 1H), 8.00 (d, 1H, J=7 Hz); $^{13}$C NMR (100 MHz, CDCl$_3$) δ 15.3, 61.7, 61.9, 98.6, 106.1, 110.7, 112.5, 121.5, 124.8, 130.2, 143.9; MS m/z 250 (M$^+$, 4), 206 (33), 177 (100), 175 (38), 159 (91), 78 (15).

Example 20

Production of imidazopyridine-8-carbaldehydes 4a-g, i

To a solution of alcohol 3a-g, i (0.56 mmol) in CHCl$_3$ (20 mL) was added MnO$_2$ (387 mg, 4.45 mmol). After refluxing, the mixture was returned back to room temperature and filtered under celite 545. The solvent was removed under reduced pressure to give carbaldehyde 4a-g, i, which was used without further purification.

Example 21

Imidazo[1,2-a]pyridine-8-carbaldehyde (4a)

From 3a, reaction time 1.5 h (yield: 85%); mp 137-139° C. (in Yamanaka, M. and al. Chem. Pharm. Bull. 1991, 39, 1556-1567: 103-104° C.); IR (KBr) 1675, 1450, 1320, 1175 cm$^{-1}$, $^1$H NMR (400 MHz, CDCl$_3$) δ 7.01 (t, 1H, J=6.5 Hz), 7.75 (s, 1H), 7.82 (s, 1H), 7.86 (d, 1H, J=6.5 Hz), 8.42 (d, 1H, J=6.5 Hz), 10.8 (s, 1H); $^{13}$C NMR (CDCl$_3$) δ 111.9, 113.3, 124.2, 126.9, 130.7, 134.9, 143.8, 188.9.

Example 22

2-Methylimidazo[1,2-a]pyridine-8-carbaldehyde (4b)

From 3b: reaction time 3 h: (yield: 98%); mp 123-125° C. (in Kaminski, J. J. and al. J. Med. Chem. 1989, 32, 1686-1700: 140-143° C.); IR (KBr) 1690, 1315 cm$^{-1}$; $^1$H NMR (400 MHz, CDCl$_3$) δ 2.49 (s, 3H), 6.86 (t, 1H, J=7 Hz), 7.44 (s, 1H), 7.71 (d, 1H, J=7 Hz), 8.26 (d, 1H, J=7 Hz), 10.66 (s, 1H); $^{13}$C NMR (100 MHz, CDCl$_3$) δ 14.5, 110.1, 111.2, 123.2, 126.2, 130.0, 143.6, 145.2, 189.0; MS m/z 160 (M$^+$, 30), 132 (100), 131 (49), 105 (25), 92 (22), 51 (20).

Example 23

2-Phenylimidazo[1,2-a]pyridine-8-carbaldehyde (4c)

From 3c, reaction time 18 h (yield: 29%); mp 98-100° C. (in Straub A. and al. U.S. Pat. No. 5,545,646, 1996: 96-99° C.); IR (KBr) 1699, 1542 cm$^{-1}$; $^1$H NMR (400 MHz, CDCl$_3$) δ 6.90 (t, 1H, J=7 Hz), 7.36 (t, 1H, J=7 Hz), 7.46 (t, 2H, J=7 Hz), 7.79 (d, 1H, J=7 Hz), 7.95 (s, 1H), 8.00 (d, 2H, J=7 Hz), 8.33 (d, 1H, J=7 Hz), 10.88 (s, 1H); $^{13}$C NMR (100 MHz, CDCl$_3$) δ 108.5, 111.9, 123.8, 125.6, 126.4, 128.6, 128.9, 130.2, 133.2, 144.7, 147.3, 189.2; MS m/z 222 (M$^+$, 45), 194 (100), 193 (84), 77 (30), 51 (31).

Example 24

2-(3-Methoxyphenyl)imidazo[1,2-a]pyridine-8-carbaldehyde (4d)

From 3d, reaction time 8 h (yield: 40%); mp 71-73° C.; IR (KBr) 1691, 1364 cm$^{-1}$; $^1$H NMR (400 MHz, CDCl$_3$) δ 3.90 (s, 3H), 6.89 (m, 2H), 7.34 (t, 1H, J=7 Hz), 7.53 (d, 1H, J=7 Hz), 7.58 (s, 1H), 7.76 (d, 1H, J=7 Hz), 7.90 (s, 1H), 8.29 (d, 1H, J=7 Hz); $^{13}$C NMR (100 MHz, CDCl$_3$) δ 55.4, 108.7, 111.5, 111.8, 114.4, 118.7, 123.7, 125.6, 129.8, 130.3, 134.5, 144.5, 147.0, 160.1, 189.1. MS m/z 252 (M$^+$, 64), 224 (100), 193 (42), 181 (18).

Example 25

2-Trifluoromethylimidazo[1,2-a]pyridine-8-carbaldehyde (4e)

From 3e: reaction time 6 h (yield: 96%); mp 98-100° C.; IR (KBr) 1709, 1164 cm$^{-1}$; $^1$H NMR (200 MHz, CDCl$_3$) δ 7.12 (t, 1H, J=7 Hz), 7.94 (d, 1H, J=7 Hz), 8.06 (s, 1H), 8.46 (d, 1H, J=7 Hz), 10.73 (s, 1H); $^{13}$C NMR (100 MHz, CDCl$_3$) δ 112.3, 113.6, 118.6 (d, $^1J_{F-C}$=267 Hz), 122.6, 124.8, 128.0, 131.1, 137.0 (q, $^2J_{F-C}$=30 Hz), 144.2, 188.0; MS m/z 214 (M$^+$, 39), 186 (100), 166 (52), 139 (25), 92 (22), 75 (55), 64 (26).

Example 26

2-iso-Propylimidazo[1,2-a]pyridine-8-carbaldehyde (4f)

From 3f: reaction time 15 h (yield: 57%); mp 70-72° C.; IR (KBr) 1669, 1540, 1500 cm$^{-1}$; $^1$H NMR (400 MHz, CDCl$_3$) δ 1.39 (d, 6H, J=7 Hz), 3.20 (sept, 1H, J=7 Hz), 6.90 (t, 1H, J=7 Hz), 7.46 (s, 1H), 7.77 (d, 1H, J=7 Hz), 8.30 (d, 1H, J=7 Hz), 10.79 (s, 1H); $^{13}$C NMR (100 MHz, CDCl$_3$) δ 22.4, 28.6, 107.9, 111.2, 123.4, 125.5, 130.2, 143.7, 156.0, 189.2; MS m/z 188 (M$^+$, 60), 173 (56), 160 (100), 145 (26), 78 (21).

Example 27

2-tert-Butylimidazo[1,2-a]pyridine-8-carbaldehyde (4g)

From 3g: reaction time 4 h (yield: 77%); mp 60-62° C.; IR (KBr) 1685, 1541, 1499 cm$^{-1}$; $^1$H NMR (400 MHz, CDCl$_3$) δ 1.43 (s, 9H), 6.86 (t, 1H, J=7 Hz), 7.46 (s, 1H), 7.76 (d, 1H, J=7 Hz), 8.28 (d, 1H, J=7 Hz), 10.85 (s, 1H); $^{13}$C NMR (100 MHz, CDCl$_3$) δ 30.2, 32.7, 107.3, 111.1, 123.5, 124.5, 130.2, 144.2, 159.0, 189.6; MS m/z 202 (M$^+$, 46), 187 (100), 174 (70), 78 (13).

Example 28

2-Diethoxymethylimidazo[1,2-a]pyridine-8-carbaldehyde (4i)

From 3i: reaction time 15 h (yield: 98%) as an oil; IR (CCl$_4$) 1693, 1056 cm$^{-1}$; $^1$H NMR (400 MHz, CDCl$_3$) δ 1.30 (t, 6H, J=7 Hz), 3.73 (m, 4H), 5.79 (s, 1H), 6.96 (t, 1H, J=7 Hz), 7.80 (s, 1H), 7.83 (d, 1H, J=7 Hz), 8.34 (d, 1H, J=7 Hz), 10.82 (s, 1H); $^{13}$C NMR (100 MHz, CDCl$_3$) δ 15.3, 62.0, 98.6, 111.0, 112.0, 124.1, 125.7, 130.6, 144.1, 146.8, 189.1; MS m/z 248 (M$^+$, 1), 204 (17), 175 (100).

Example 29

2-Bromoimidazo[1,2-a]pyridine-8-carbaldehyde (4j—According to Chezal, J. M. and al. J. Org. Chem. 2001, 66, 6576-6584)

To a solution of potassium carbonate (0.60 g) in water (50 mL) was added 3-bromo-8-dibromomethyleneimidazo[1,2-a]pyridine (5) (0.60 g, 1.63 mmol, Chezal, J. M. and al. J. Org. Chem. 2001, 66, 6576-6584). The reaction mixture was stirred at reflux for 4 h. The mixture was returned back to room temperature and extracted with CH$_2$Cl$_2$. The organic layers were dried (Na$_2$SO$_4$), filtered and removed under reduced pressure. The residue was purified by chromatography using CH$_2$Cl$_2$ as eluent to give 4j (0.21 g, 55%); mp 203-205° C.; IR (KBr) 1670, 1530, 1455, 1270, 720 cm$^{-1}$; $^1$H NMR (400 MHz, CDCl$_3$) δ 7.02 (t, 1H, J=7H), 7.72 (s, 1H), 7.85 (d, 1H, J=7 Hz), 8.31 (d, 1H, J=7 Hz), 10.73 (s, 1H); $^{13}$C NMR (100 MHz, CDCl$_3$) δ 112.7, 113.1, 123.8, 124.7, 126.7, 129.9, 144.4, 188.7; MS m/z 226 (M$^+$+2, 43), 224 (M$^+$, 43), 198 (98), 196 (100), 117 (50), 92 (40), 63 (26), 51 (17).

Example 30

Bromination of aldehydes 4a, b

To a solution of the appropriate aldehyde (1.39 mmol) in AcOH (6 mL) was added dropwise a solution of bromine (266 mg, 1.66 mmol) in AcOH (3 mL). The solution was stirred at room temperature for 3.5 h. The solution was diluted with water (6 mL), cooled to 0° C. and made basic by the addition of aqueous saturated $Na_2CO_3$ solution (30 mL) over 20 min. The solution was extracted with $CH_2Cl_2$ and the combinated extracts were dried ($MgSO_4$), filtered and evaporated under reduced pressure to give bromo compound.

Example 31

3-Bromoimidazo[1,2-a]pyridine-8-carbaldehyde (4k)

From 4a (yield: 35%); mp 104-106° C.; IR (KBr) 1694, 1186 cm$^{-1}$; $^1$H NMR (400 MHz, CDCl$_3$) δ 7.09 (t, 1H J=7 Hz), 7.74 (s, 1H), 7.86 (d, 1H, J=7 Hz), 8.32 (d, 1H, J=7 Hz), 10.66 (s, 1H); $^{13}$C NMR (100 MHz, CDCl$_3$) δ 96.4, 112.9, 124.2, 127.1, 128.5, 134.6, 144.2, 188.2; MS m/z 226 (M$^+$+2, 45), 224 (M$^+$, 46), 198 (99), 196 (100), 117 (76), 90 (54), 63 (30).

Example 32

3-Bromo-2-methylimidazo[1,2-a]pyridine-8-carbaldehyde (4l)

From 4b (yield: 68%); mp 137-139° C.; IR (KBr) 1695, 1541 cm$^{-1}$; $^1$H NMR (400 MHz, CDCl$_3$) δ 2.55 (s, 3H), 7.08 (t, 1H, J=7 Hz), 7.87 (d, 1H, J=7 Hz), 8.30 (d, 1H, J=7 Hz), 10.72 (s, 1H); $^{13}$C NMR (100 MHz, CDCl$_3$) δ 13.7, 94.6, 112.3, 123.3, 126.8, 128.4, 143.6, 143.7, 188.3; MS m/z 240 (M$^+$+2, 66), 238 (M$^+$, 67), 212 (98), 210 (100), 131 (77), 104 (73), 78 (33), 51 (40).

Example 33

2-Methyl-3-nitroimidazo[1,2-a]pyridine-8-carbaldehyde (4m)

To a cooled solution of 4a (149 mg, 0.93 mmol) in concentrated sulfuric acid (4 mL), was added nitric acid (155 μl, d=1.38). After being stirred for 3 h at room temperature, the solution is crushed on ice (10g), made basic by the addition of aqueous saturated $Na_2CO_3$ solution (45 mL) and extracted with $CH_2Cl_2$. The organic layers were dried ($MgSO_4$), filtered and evaporated to dryness to give 4m (171 mg, 90%); mp 182-184° C.; IR (KBr) 1698, 1380, 1134 cm$^{-1}$; $^1$H NMR (400 MHz, CDCl$_3$) δ 2.95 (s, 3H), 7.40 (t, 1H, J=7 Hz), 8.21 (d, 1H, J=7 Hz), 9.66 (d, 1H, J=7 Hz), 10.83 (s, 1H); $^{13}$C NMR (100 MHz, CDCl$_3$) δ 17.4, 115.7, 123.4, 130.3, 130.4, 131.9, 144.3, 152.0, 187.3; MS m/z 205 (M$^+$, 31), 177 (100), 104 (40), 78 (37), 51 (33).

Example 34

Preparation of ethyl imidazopyridine propenoate (According to the Literature Method: Chezal, J. M. and al. *J. Org. Chem.* 2001, 66, 6576-6584)

Ethyl azidoacetate (1.81 g, 14.0 mmol) was added dropwise at −30° C. to a stirred solution containing sodium (0.20 g, 8.70 mmol) in dry ethanol (10 mL). To this solution was added dropwise a solution of aldehyde 4 (1.00 mmol) in dry ethanol (8 mL). The reaction mixture was returned back room temperature and stirred for 3 h (CAUTION: an exothermic reaction can take place, with gas expansion). The solution was poured into aqueous saturated ammonium chloride solution (30 mL) and then extracted with $CH_2Cl_2$. The organic layers were dried ($Na_2SO_4$), filtered and evaporated in vacuo. The crude product was purified by chromatography using $CH_2Cl_2$ as eluent to afford the azide derivative 6.

Example 35

Ethyl α-azido-β-(imidazo[1,2-a]pyridin-8-yl)propenoate (6a)

From 4a (yield: 10%); mp: 150-152° C.; IR (KBr) 2100, 1700, 1600, 1280 cm$^{-1}$; $^1$H NMR (400 MHz, CDCl$_3$) δ 1.41 (t, 3H, J=7 Hz), 4.39 (q, 2H, J=7 Hz), 6.83 (t, 1H, J=7 Hz), 7.57 (d, 1H, J=1 Hz), 7.61 (d, 1H, J=1 Hz), 7.76 (s, 1H), 8.06 (dd, 1H, J=7, 1 Hz), 8.17 (dd, 1H, J=7, 1 Hz). MS m/z 257 (M$^+$, 1), 229 (61), 183 (100), 155 (31), 129 (23), 104 (14). Further elution gave 8-methylimidazo[1,2-a]pyridine (yield: 10%-Kaiser, C. and al. *J. Med. Chem.* 1992, 35, 4415-4424).

Example 36

Ethyl α-azido-β-(2-methylimidazo[1,2-a]pyridin-8-yl)propenoate (6b)

From 4b (yield: 32%); mp 121-123° C., IR (KBr) 2132, 1702, 1283 cm$^{-1}$; $^1$H NMR (200 MHz, CDCl$_3$) δ 1.43 (t, 1H, J=7 Hz), 2.49 (s, 3H), 4.40 (q, 2H, J=7 Hz), 6.81 (t, 1H, J=7 Hz), 7.36 (s, 1H), 7.73 (s, 1H), 8.00 (d, 1H, J=7 Hz), 8.14 (d, 1H, J=7 Hz); MS m/z 271 (M$^+$, 1), 243 (55), 197 (100), 169 (8), 143 (20), 55 (19).

Example 37

Ethyl α-azido-β-(2-phenylimidazo[1,2-a]pyridin-8-yl)propenoate (6c)

From 4c (yield: 31%); mp 136-138° C.; IR (KBr) 2103, 1712, 1266 cm$^{-1}$; $^1$H NMR (400 MHz, CDCl$_3$) δ 1.47 (t, 3H, J=7 Hz), 4.43 (q, 2H, J=7 Hz), 6.83 (t, 1H, J=7 Hz), 7.34 (t, 1H, J=7.5 Hz), 7.45 (t, 2H, J=7.5 Hz), 7.85 (s, 1H), 7.90 (s, 1H), 8.00 (d, 2H, J=7.5 Hz), 8.05 (d, 1H, J=7 Hz), 8.18 (d, 1H, J=7 Hz); MS m/z 333 (M$^+$, 2), 305 (59), 259 (100), 102 (48).

Example 38

Ethyl α-azido-β-(2-(3-methoxyphenyl)imidazo[1,2-a]pyridin-8-yl)propenoate (6d)

From 4d (yield: 9%); mp 109-111° C.; IR (KBr) 2107, 1704, 1252 cm$^{-1}$; $^1$H NMR (200 MHz, CDCl$_3$) δ 1.45 (t, 3H, J=7 Hz), 3.91 (s, 3H), 4.44 (q, 2H, J=7 Hz), 6.88 (m, 2H), 7.35 (t, 1H, J=8 Hz), 7.55 (d, 1H, J=8 Hz), 7.60 (s, 1H), 7.85 (s, 1H), 7.89 (s, 1H), 8.05 (d, 1H, J=7 Hz), 8.18 (d, 1H, J=7 Hz).

Example 39

Ethyl α-azido-β-(2-trifluoromethylimidazo[1,2-a]pyridin-8-yl)propenoate (6e)

From 4e (yield: 49%); mp 140-142° C.; IR (KBr) 2100, 1740, 1262, 1107 cm$^{-1}$; $^1$H NMR (200 MHz, CDCl$_3$) δ 1.43 (t, 3H, J=7 Hz), 4.41 (q, 2H, J=7 Hz), 6.98 (t, 1H, J=7 Hz), 7.69 (s, 1H), 7.91 (s, 1H), 8.10 (d, 1H, J=7 Hz), 8.31 (d, 1H, J=7 Hz); MS m/z 325 (M$^+$, 2), 297 (64), 251 (100), 223 (28), 154 (21), 57 (34).

Example 40

Ethyl α-azido-β-(2-isopropylimidazo[1,2-a]pyridin-8-yl)propenoate (6f)

From 4f (yield: 68%); mp 66-68° C.; IR (KBr) 2105, 1695, 1324, 1262 cm$^{-1}$; $^1$H NMR (200 MHz, CDCl$_3$) δ 1.39 (m, 9H), 3.14 (sept, 1H, J=7 Hz), 4.31 (q, 2H, J=7 Hz), 6.80 (t, 1H, J=7 Hz), 7.35 (s, 1H), 7.77 (s, 1H), 8.01 (d, 1H, J=7 Hz), 8.14 (d, 1H, J=7 Hz); MS m/z 299 (M$^+$, 2), 271 (66), 256 (29), 225 (36), 210 (100), 183 (28).

Example 41

Ethyl α-azido-β-(2-tert-butylimidazo[1,2-a]pyridin-8-yl)propenoate (6g)

From 4g: (yield: 52%); mp 108-110° C.; IR (KBr) 2109, 1704, 1259 cm$^{-1}$; $^1$H NMR (200 MHz, CDCl$_3$) δ 1.40 (m, 12H), 4.53 (q, 2H, J=7 Hz), 6.77 (t, 1H, J=7 Hz), 7.35 (s, 1H), 7.82 (s, 1H), 8.00 (d, 1H, J=7 Hz), 8.11 (d, 1H, J=7 Hz); MS m/z 313 (M$^+$, 1), 285 (47), 270 (33), 224 (100).

Example 42

Ethyl α-azido-β-(2-diethoxymethylimidazo[1,2-a]pyridin-8-yl)propenoate (6h)

From 4i (yield: 28%) as an oil; IR (CCl$_4$) 2127, 1751, 1204 cm$^{-1}$; $^1$H NMR (200 MHz, CDCl$_3$) δ 1.26 (t, 6H, J=7 Hz), 1.40 (t, 3H, J=7 Hz), 3.70 (m, 4H), 4.35 (q, 2H, J=7 Hz), 5.76 (s, 1H), 6.83 (t, 1H, J=7 Hz), 7.67 (s, 1H), 7.76 (s, 1H), 8.04 (d, 1H, J=7 Hz), 8.17 (d, 1H, J=7 Hz).

Example 43

Ethyl α-azido-β-(2-bromoimidazo[1,2-a]pyridin-8-yl)propenoate (6i) (in Chezal, J. M. and al. J. Org. Chem. 2001, 66, 6576-6584)

From 4j (yield: 64%); mp 149-151° C.; IR (KBr) 2050, 1685, 1460, 1260, 735 cm$^{-1}$; $^1$H NMR (400 MHz, CDCl$_3$) δ 1.42 (t, 3H, J=7 Hz), 4.39 (q, 2H, J=7 Hz), 6.88 (t, 1H, J=7 Hz), 7.57 (s, 1H), 7.65 (s, 1H), 8.00 (d, 1H, J=7 Hz), 8.20 (d, 1H, J=7 Hz); MS m/z 337 (M$^+$+2, 3), 335 (M$^+$, 4), 309 (37), 307 (35), 263 (48), 261 (50), 237 (17), 235 (19), 149 (92), 57 (100).

Example 44

Ethyl α-azido-β-(3-bromoimidazo[1,2-a]pyridin-8-yl)propenoate (6j)

From 4k (yield: 33%); mp 90-92° C.; IR (KBr) 2110, 1707, 1299, 1260 cm$^{-1}$; $^1$H NMR (200 MHz, CDCl$_3$) δ 1.45 (t, 3H, J=7 Hz), 4.43 (q, 2H, J=7 Hz), 7.12 (t, 1H, J=7 Hz), 7.70 (s, 1H), 7.79 (s, 1H), 8.13 (d, 1H, J=7 Hz), 8.38 (d, 1H, J=7 Hz); MS m/z 337 (M$^+$+2, 5), 335 (M$^+$, 5), 309 (67), 307 (64), 263 (100), 261 (95), 235 (42), 156 (69), 154 (70), 129 (36).

Example 45

Ethyl α-azido-β-(3-bromo-2-methylimidazo[1,2-a]pyridin-8-yl)propenoate (6k)

From 4l (yield: 22%); mp 108-110° C.; IR (KBr) 2113, 1720, 1331 cm$^{-1}$; $^1$H NMR (200 MHz, CDCl$_3$) δ 1.44 (t, 3H, J=7 Hz), 2.50 (s, 3H), 4.41 (q, 2H, J=7 Hz), 6.98 (t, 1H, J=7 Hz), 7.71 (s, 1H), 8.02 (d, 1H, J=7 Hz), 8.24 (d, 1H, J=7 Hz); MS m/z 323 (M$^+$+2-28, 47), 321 (M$^+$-28, 47), 277 (98), 275 (100), 168 (40).

Example 46

Ethyl α-azido-β-(2-methyl-3-nitroimidazo[1,2-a]pyridin-8-yl)propenoate (6l). From 4m (yield: 29%); mp 196-198° C.; IR (KBr) 2124, 1713, 1374, 1306, 1246 cm$^{-1}$; $^1$H NMR (200 MHz, CDCl$_3$) δ 1.44 (t, 3H, J=7 Hz), 2.90 (s, 3H), 4.44 (q, 2H, J=7 Hz), 7.29 (t, 1H, J=7 Hz), 7.70 (s, 1H), 8.59 (d, 1H, J=7 Hz), 9.36 (d, 1H, J=7 Hz); MS m/z 316 (M$^+$, 2), 288 (100), 143 (54).

Example 47

Thermolysis of Azidopropenoate Compounds

A solution of azide 6 (0.29 mmol) in chlorobenzene (10 mL) was stirred at reflux for 10 min. After cooling, the solution was concentrated in vacuo to dryness. The residual material was washed with ether (3 mL) to give the cyclized compound 7.

Example 48

Ethyl imidazo[1,2-a]pyrrolo[3,2-c]pyridine-8-carboxylate (7a)

From 6a (yield: 84%); mp 154-156° C.; IR (KBr) 3276, 2924, 1684, 1252 cm$^{-1}$; $^1$H NMR (400 MHz, CDCl$_3$) δ 1.38 (t, 3H, J=7 Hz), 4.38 (q, 2H, J=7 Hz), 7.05 (d, 1H, J=7 Hz), 7.36 (s, 1H), 7.40 (s, 1H), 7.88 (s, 1H), 8.32 (d, 1H, J=7 Hz), 12.53 (brs, 1H); $^{13}$C NMR (100 MHz, CDCl$_3$) δ 14.3, 60.4, 101.5, 106.5, 113.5, 113.7, 124.5, 125.6, 130.3, 133.0, 140.7, 160.6; MS m/z 229 (M$^+$, 73), 183 (100), 155 (20), 129 (9). Anal. Calcd for C$_{12}$H$_{11}$N$_3$O$_2$: C, 62.87; H, 4.84; N, 18.33. Found: C, 63.11; H, 4.75; N, 18.22.

Example 49

Ethyl 2-methylimidazo[1,2-a]pyrrolo[3,2-c]pyridine-8-carboxylate (7b)

From 6b (yield: 52%); mp 201-203° C., IR (KBr) 3280, 1680, 1250 cm$^{-1}$; $^1$H NMR (400 MHz, CDCl$_3$) δ 1.39 (t, 1H, J=7 Hz), 2.48 (s, 3H), 4.40 (q, 2H, J=7 Hz), 6.86 (d, 1H, J=7 Hz), 7.23 (s, 1H), 7.62 (s, 1H), 7.80 (d, 1H, J=7 Hz), 10.01 (brs, 1H); $^{13}$C NMR (100 MHz, CDCl$_3$) δ 14.1, 14.3, 61.1, 100.6, 107.9, 109.7, 114.4, 123.2, 126.3, 132.6, 140.6, 141.1, 161.6; MS m/z 243 (M$^+$, 44), 197 (100), 169 (22), 168 (21), 143 (27). Anal. Calcd for $C_{13}H_{13}N_3O_2$: C, 64.19; H, 5.39; N, 17.27. Found: C, 64.44; H, 5.58; N, 17.34.

Example 50

Ethyl 2-phenylimidazo[1,2-a]pyrrolo[3,2-c]pyridine-8-carboxylate (7c)

From 6c (yield: 90%); mp 255-257° C.; IR (KBr) 3266, 1676, 1253 cm$^{-1}$; $^1$H NMR (400 MHz, DMSO-d$_6$) δ 1.39 (t, 3H, J=7 Hz), 4.39 (q, 2H, J=7 Hz), 7.07 (d, 1H, J=7.5 Hz), 7.32 (t, 1H, J=7.5 Hz), 7.47 (m, 3H), 7.99 (d, 2H, J=7.5 Hz), 8.31 (d, 1H, J=7.5 Hz), 8.33 (s, 1H), 12.6 (s, 1H); $^{13}$C NMR (100 MHz, DMSO-d$_6$) δ 14.3, 60.4, 101.7, 106.7, 109.6, 113.2, 124.3, 125.2, 125.8, 127.1, 128.6, 133.2, 134.2, 141.1, 142.0, 160.5; MS m/z 305 (M$^+$, 40), 259 (100), 102 (48). Anal. Calcd for $C_{18}H_{15}N_3O_2$: C, 70.81; H, 4.95; N, 13.76. Found: C, 71.02; H, 4.88; N, 13.87.

Example 51

Ethyl 2-(3-methoxyphenyl)imidazo[1,2-a]pyrrolo[3,2-c]pyridine-8-carboxylate (7d)

From 6d (yield: 50%); mp 198-200° C.; IR (KBr) 3297, 1670, 1261 cm$^{-1}$; $^1$H NMR (400 MHz, DMSO-d$_6$) δ 1.41 (t, 3H, J=7 Hz), 3.90 (s, 3H), 4.41 (q, 2H, J=7 Hz), 6.88 (m, 2H), 7.34 (t, 1H, J=8 Hz), 7.52 (d, 2H, J=8 Hz), 7.58 (s, 1H), 7.74 (s, 1H), 7.76 (s, 1H), 7.88 (d, 1H, J=7 Hz), 9.93 (brs, 1H); $^{13}$C NMR (100 MHz, DMSO-d$_6$) δ 14.3, 54.9, 60.5, 101.8, 106.8, 110.0, 110.4, 112.9, 113.2, 117.6, 124.3, 125.9, 129.7, 133.2, 135.6, 141.0, 141.9, 159.6, 160.6; MS m/z 335 (M$^+$, 69), 289 (100), 132 (15), 102 (17). Anal. Calcd for $C_{19}H_{17}N_3O_3$: C, 68.05; H, 5.11; N, 12.53. Found: C, 68.23; H, 5.04; N, 12.73.

Example 52

Ethyl 2-trifluoromethylimidazo[1,2-a]pyrrolo[3,2-c]pyridine-8-carboxylate (7e)

From 6e (yield: 79%); mp 230-231° C.; IR (KBr) 3283, 1686, 1264 cm$^{-1}$; $^1$H NMR (400 MHz, acetone-d$_6$) δ 1.43 (t, 3H, J=7 Hz), 4.43 (q, 2H, J=7 Hz), 7.33 (d, 1H, J=7 Hz), 7.55 (s, 1H), 8.33 (s, 1H), 8.37 (d, 1H, J=7 Hz), 11.74 (brs, 1H); $^{13}$C NMR (100 MHz, acetone-d$_6$) δ 14.6, 61.5, 104.3, 107.9, 114.2, 114.8, 124.4 (d, $^1J_{F-C}$=266 Hz), 125.3, 127.9, 133.8 (q, $^2J_{F-C}$=37 Hz), 134.4, 143.1; 161.4; MS m/z 297 (M$^+$, 66), 251 (100), 223 (27), 154 (14). Anal. Calcd for $C_{13}H_{10}F_3N_3O_2$: C, 52.53; H, 3.39; N, 14.14. Found: C, 52.78; H, 3.46; N, 14.02.

Example 53

Ethyl 2-isopropylimidazo[1,2-a]pyrrolo[3,2-c]pyridine-8-carboxylate (7f)

From 6f (yield: 87%); mp 207-209° C.; IR (KBr) 3285, 1681, 1248 cm$^{-1}$; $^1$H NMR (400 MHz, CDCl$_3$) δ 1.30 (t, 3H, J=7 Hz), 1.34 (d, 6H, J=7 Hz), 3.11 (sept, 1H, J=7 Hz), 4.42 (q, 2H, J=7 Hz), 6.82 (d, 1H, J=7 Hz), 7.17 (s, 1H), 7.56 (s, 1H), 7.73 (d, 1H, J=7 Hz), 11.40 (brs, 1H); $^{13}$C NMR (100 MHz, CDCl$_3$) δ 14.2, 22.5, 28.3, 61.0, 101.0, 107.5, 108.1, 114.1, 123.3, 126.2, 133.2, 141.31, 151.4, 161.9; MS m/z 271 (M$^+$, 82), 256 (40), 225 (42), 210 (100), 182 (20). Anal. Calcd for $C_{15}H_{17}N_3O_2$: C, 66.40; H, 6.32; N, 15.49. Found: C, 66.68; H, 6.41; N, 15.57.

Example 54

Ethyl 2-tert-butylimidazo[1,2-a]pyrrolo[3,2-c]pyridine-8-carboxylate (7g)

From 6g (yield: 57%); mp 276-278° C.; IR (KBr) 1711, 1243, 1175 cm$^{-1}$; $^1$H NMR (400 MHz, DMSO-d$_6$) δ 1.38 (m, 12H), 4.36 (q, 2H, J=7 Hz), 6.97 (d, 1H, J=7 Hz), 7.36 (s, 1H), 7.56 (s, 1H), 8.21 (d, 1H, J=7 Hz), 12.43 (brs, 1H); $^{13}$C NMR (100 MHz, DMSO-d$_6$) δ 14.2, 30.1, 31.8, 60.3, 100.6, 106.6, 107.2, 113.2, 124.2, 125.5, 124.2, 125.5, 133.0, 140.1, 153.2, 160.6; MS m/z 285 (M$^+$, 57), 270 (38), 224 (100), 196 (17). Anal. Calcd for $C_{16}H_{19}N_3O_2$: C, 67.35; H, 6.71; N, 14.73. Found: C, 67.20; H, 6.88; N, 14.51.

Example 55

Ethyl 2-diethoxymethylimidazo[1,2-a]pyrrolo[3,2-c]pyridine-8-carboxylate (7h)

From 6h (yield: 97%); mp 242-244° C.; IR (KBr) 3422, 1719, 1252, 1190 cm$^{-1}$; $^1$H NMR (400 MHz, CDCl$_3$) δ 1.26 (t, 6H, J=7 Hz), 1.37 (t, 3H, J=7 Hz), 3.71 (m, 4H), 4.38 (q, 2H, J=7 Hz), 6.96 (d, 1H, J=7 Hz), 7.58 (s, 1H), 7.65 (s, 1H), 7.84 (d, 1H, J=7 Hz), 10.40 (brs, 1H); $^{13}$C NMR (100 MHz, CDCl$_3$) δ 14.3, 15.3, 61.1, 61.8, 98.8, 101.8, 108.3, 111.0, 114.5, 123.5, 126.4, 132.8, 141.5, 142.6, 161.6; MS m/z 331 (M$^+$, 1), 257 (61), 211 (78), 183 (33), 99 (38), 85 (65), 71 (81), 57 (100). Anal. Calcd for $C_{17}H_{21}N_3O_4$: C, 61.62; H, 6.39; N, 12.68. Found: C, 61.27; H, 6.31; N, 12.79.

Example 56

Ethyl 2-bromoimidazo[1,2-a]pyrrolo[3,2-c]pyridine-8-carboxylate (7i) (in Chezal, J. M. and al. J. Org. Chem. 200466, 6576-6584)

From 6i (yield: 98%); 266-268° C.; IR (KBr) 3280, 1680, 1240, 1180 cm$^{-1}$; $^1$H NMR (400 MHz, DMSO-d$_6$) δ δ 1.36 (t, 3H, J=7 Hz), 4.35 (q, 2H, J=7 Hz), 7.10 (d, 1H, J=7.5 Hz), 7.34 (s, 1H), 8.01 (s, 1H), 8.25 (d, 1H, J=7.5 Hz), 10.97 (s, 1H); $^{13}$C NMR (100 MHz, DMSO-d$_6$) δ 14.29, 60.59, 102.27, 106.40, 112.20, 112.50, 117.96, 123.74, 126.29, 133.20, 140.66, 160.49; MS m/z 309 (M$^+$+2, 48), 307 (M$^+$, 44), 263 (92), 261 (92), 154 (100), 127 (34), 100 (30), 76 (40), 52 (34). Anal. Calcd for $C_{12}H_{10}BrN_3O_2$: C, 46.78; H, 3.27; N, 13.64. Found: C, 46.44; H, 3.42; N, 13.32.

Example 57

Ethyl 3-bromoimidazo[1,2-a]pyrrolo[3,2-c]pyridine-8-carboxylate (7j)

From 6j (yield: 92%); mp 280-282° C.; IR (KBr) 1707, 1178 cm$^{-1}$; $^1$H NMR (400 MHz, DMSO-d$_6$) δ 1.39 (t, 3H, J=7 Hz), 4.39 (q, 2H, J=7 Hz), 7.23 (d, 1H, J=7 Hz), 7.40 (s, 1H), 7.56 (s, 1H), 8.13 (d, 1H, J=7 Hz), 12.69 (brs, 1H); $^{13}$C NMR (100 MHz, DMSO-d$_6$) δ 14.3, 60.6, 94.9, 102.9, 106.1, 113.5, 121.6, 126.4, 130.7, 132.9, 141.6, 160.5; MS m/z 309 (M$^+$+2, 57), 307 (M$^+$, 57), 263 (100), 261 (88), 154 (58). Anal. Calcd for $C_{12}H_{10}BrN_3O_2$: C, 46.78; H, 3.27; N, 13.64. Found: C, 46.89; H, 3.40; N, 13.57.

Example 58

Ethyl 3-bromo-2-methylimidazo[1,2-a]pyrrolo[3,2-c]pyridine-8-carboxylate (7k)

From 6k (yield: 98%); mp 224-226° C.; IR (KBr) 3288, 1685, 1258, 1188 cm$^{-1}$; $^1$H NMR (400 MHz, CDCl$_3$) δ 1.40

(t, 3H, J=7 Hz), 2.46 (s, 3H), 4.41 (q, 2H, J=7 Hz), 6.99 (d, 1H, J=7 Hz), 7.62 (s, 1H), 7.84 (d, 1H, J=7 Hz), 10.27 (brs, 1H); $^{13}$C NMR (100 MHz, CDCl$_3$) δ 13.4, 14.3, 61.3, 93.2, 101.3, 107.4, 114.3, 121.7, 126.8, 132.8, 139.0, 141.4, 161.6; MS m/z 323 (M$^+$+2, 50), 321 (M$^+$, 49), 277 (100), 275 (97), 168 (24). Anal. Calcd for C$_{13}$H$_{12}$BrN$_3$O$_2$: C, 48.47; H, 3.75; N, 13.04. Found: C, 48.15; H, 3.88; N, 12.97.

Example 59

Ethyl 2-methyl-3-nitroimidazo[1,2-a]pyrrolo[3,2-c]pyridine-8-carboxylate (7l)

From 6l (yield: 66%); mp 300-302° C.; IR (KBr) 3291, 1682, 1351, 1163 cm$^{-1}$; $^1$H NMR (400 MHz, DMSO-d$_6$) δ 1.40 (t, 3H, J=7 Hz), 2.78 (s, 3H), 4.41 (q, 2H, J=7 Hz), 7.50 (d, 1H, J=7 Hz), 7.55 (s, 1H), 9.17 (d, 1H, J=7 Hz), 13.04 (brs, 1H); $^{13}$C NMR (100 MHz, DMSO-d$_6$) δ 14.2, 17.2, 61.0, 104.4, 106.9, 112.7, 124.1, 128.5, 135.5, 141.4, 149.8, 160.1, one carbon not observed; MS m/z 288 (M$^+$, 100), 242 (31), 225 (27), 189 (29), 143 (49), 115 (21). Anal. Calcd for C$_{13}$H$_{12}$N$_4$O$_4$: 54.17; H, 4.20; N, 19.44. Found: C, 54.38; H, 4.10; N, 19.71.

Example 60

Ethyl 2-formylimidazo[1,2-a]pyrrolo[3,2-c]pyridine-8-carboxylate (8)

To a solution of 7h (249 mg, 0.75 mmol) in a solution of CH$_3$CN/H$_2$O (3/1, v/v, 20 mL) was added a small quantity of concentrated HCl (3 drops). The solution was stirred at room temperature for 24 h. The reaction mixture was basified with aqueous saturated Na$_2$CO$_3$ solution (8 mL) and extracted with CH$_2$Cl$_2$ (3×20 mL). The extracts were dried (MgSO$_4$), filtered and evaporated to give compound 9 (163 mg, 84%); mp 242-244° C.; IR (KBr) 3230, 1740, 1668 cm$^{-1}$; $^1$H NMR (400 MHz, DMSO-d$_6$) δ 1.39 (t, 3H, J=7 Hz), 4.39 (q, 2H, J=7 Hz), 7.20 (d, 1H, J=7 Hz), 7.44 (s, 1H), 8.38 (d, 1H, J=7 Hz), 8.66 (s, 1H), 10.02 (s, 1H), 11.74 (brs, 1H); $^{13}$C NMR (100 MHz, DMSO-d$_6$) δ 14.2, 60.6, 104.1, 107.1, 113.1, 120.8, 124.8, 126.2, 133.4, 141.6, 142.0, 160.4, 186.7; MS m/z 257 (M$^+$, 78), 211 (100), 183 (35), 143 (29), 129 (26), 57 (28). Anal. Calcd for C$_{13}$H$_{11}$N$_3$O$_3$: C, 60.70; H, 4.31; N, 16.33. Found: C, 60.52; H, 4.63; N, 16.28.

Example 61

Ethyl 2-N,N dimethylaminomethylimidazo[1,2-a]pyrrolo[3,2-c]pyridine-8-carboxylate (9)

To a solution of 8 (64 mg, 0.25 mmol) in dry MeOH (5 mL), under argon, were added dimethylamine hydrochloride (62 mg, 0.76 mmol) and triethylamine (106 µl, 0.76 mmol). The mixture was stirred at room temperature for 15 min in a closed vessel then NaBH$_3$CN was added (17 mg, 0.27 mmol). After stirring for 2 h at room temperature the solvent was evaporated in vacuo. The residue was diluted with water (10 mL) and extracted with CH$_2$Cl$_2$. The organic layers were dried (MgSO$_4$), filtered and evaporated under reduced pressure. The residue was purified by chromatography using CH$_2$Cl$_2$/EtOH (97/3, v/v) as eluent to give compound 8 (31 mg, 41%); mp 82-84° C.; IR (KBr) 3422, 1701, 1247, 1189 cm$^{-1}$; $^1$H NMR (400 MHz, CDCl$_3$) δ 1.37 (t, 3H, J=7 Hz), 2.44 (s, 6H), 3.77 (s, 2H), 4.37 (q, 2H, J=7 Hz), 6.90 (d, 1H, J=7 Hz), 7.49 (s, 1H), 7.60 (s, 1H), 7.78 (d, 1H, J=7 Hz), 10.57 (brs, 1H); $^{13}$C NMR (100 MHz, CDCl$_3$) δ 14.3, 45.0, 57.1, 61.1, 101.4, 108.1, 111.8, 114.4, 123.4, 126.3, 132.8, 140.5, 141.5, 161.6; MS m/z 286 (M$^+$, 3), 243 (62), 197 (100). Anal. Calcd for C$_{15}$H$_{18}$N$_4$O$_2$: C, 62.92; H, 6.34; N, 19.57. Found: C, 63.15; H, 6.23; N, 19.31.

Example 62

2-Bromo-8-hydroxymethylimidazo[1,2-a]pyrrolo[3,2-c]pyridine (10)

To a solution of ester 7i (50 mg, 0.16 mmol) in dry CH$_2$Cl$_2$ (7 mL) at −80° C., under argon, was added DIBAL-H (1.60 mL, 1M in hexanes). The solution was stirred at −80° C. for 45 min and DIBAL-H (1.60 mL) was added. After 45 min at −80° C. the reaction was quenched by addition of MeOH (1 mL) and 3% aqueous NaOH solution (100 mL). The reaction was returned back to room temperature, filtered under celite 545 and washed with CH$_2$Cl$_2$/EtOH (9/1, v/v, 10 mL). The solvent was removed from the filtrate under reduced pressure. The residue was purified by chromatography using CH$_2$Cl$_2$/EtOH (9/1, v/v) as eluent to afford in order of elution: starting material 7i (10 mg); compound 10 (17 mg, 39%); mp 113-115° C.; IR (KBr) 3230, 1740, 1668 cm$^{-1}$; $^1$H NMR (400 MHz, CD$_3$OD) δ 4.63 (s, 2H), 6.65 (s, 1H), 6.96 (d, 1H, J=7 Hz), 7.60 (s, 1H), 7.86 (d, 1H, J=7 Hz); MS m/z 267 (M$^+$+2, 24), 265 (M+, 25), 249 (26), 247 (26), 187 (, 100), 169 (55), 143 (17), 129 (17), 117 (21). Anal. Calcd for C$_{10}$H$_8$BrN$_3$O: C, 45.14; H, 3.03; N, 15.79. Found: C, 45.21; H, 3.17; N, 15.91.

Example 63

Ethyl 2-hydroxymethylimidazo[1,2-a]pyrrolo[3,2-c]pyridine-8-carboxylate (11)

To a solution of 8 (40 mg, 0.16 mmol) in dry ethanol (5 mL), under argon, was added NaBH$_4$ (9 mg, 0.24 mmol). The solution was stirred at room temperature for 30 min then the solvent was removed in vacuo. An aqueous saturated Na$_2$CO$_3$ solution (5 mL) was added and the solution was extracted with CH$_2$Cl$_2$ (3×20 mL). The organic layers were dried (MgSO$_4$), filtered and evaporated to give compound 11 (23 mg, 57%); mp 227-229° C.; IR (KBr) 3289, 1685, 1266, 1191 cm$^{-1}$; $^1$H NMR (400 MHz, DMSO-d$_6$) δ 1.38 (t, 3H, J=7 Hz), 4.38 (q, 2H, J=7 Hz), 4.60 (s, 2H), 5.17 (brs, 1H), 7.01 (d, 1H, J=7 Hz), 7.33 (s, 1H), 7.72 (s, 1H), 8.29 (d, 1H, J=7 Hz), 12.50 (brs, 1H); $^{13}$C NMR (100 MHz, DMSO-d$_6$) δ 14.3, 58.0, 60.4, 101.1, 106.4, 110.3, 113.1, 124.4, 125.6, 133.1, 140.2, 144.7, 160.5; MS m/z 259 (M$^+$, 60), 213 (52), 212 (100), 184 (22), 57 (25). Anal. Calcd for C$_{13}$H$_{13}$N$_3$O$_3$: C, 60.22; H, 5.05; N, 16.21. Found: C, 60.13; H, 5.18; N, 16.02.

Example 64

Ethyl 2-chloromethylimidazo[1,2-a]pyrrolo[3,2-c]pyridine-8-carboxylate (12)

To a solution of 11 (47 mg, 0.18 mmol) in dry methylene chloride (10 mL), under argon, were added SOCl$_2$ (15 µl, 0.21 mmol) and triethylamine (29 µl, 0.21 mmol). The solution was stirred at room temperature for 45 min then the solvent was removed in vacuo. The crude product was purified by chromatography using CH$_2$Cl$_2$/EtOH (97/3, v/v) as eluent to give compound 12 (26 mg, 52%); mp 270-272° C.; IR (KBr) 1701, 1248, 1189 cm$^{-1}$; $^1$H NMR (400 MHz, acetone-d$_6$) δ 1.41 (t, 3H, J=7 Hz), 4.41 (q, 2H, J=7 Hz), 4.86 (s, 2H), 7.20 (d, 1H, J=7 Hz), 7.52 (s, 1H), 7.90 (s, 1H), 8.28 (d, 1H, J=7 Hz), 11.63 (brs, 1H); $^{13}$C NMR (100 MHz, (acetone-d$_6$) δ

14.7, 40.6, 61.3, 102.9, 107.9, 113.1, 114.7, 125.0, 127.5, 134.3, 140.9, 142.3, 161.5; MS m/z 279 (M$^+$+2, 9), 277 (M$^+$, 20), 196 (43), 149 (33), 85 (63), 71 (72), 57 (100). Anal. Calcd for $C_{13}H_{12}ClN_3O_2$: C, 56.22; H, 4.36; N, 15.13. Found: C, 56.07; H, 4.43; N, 15.10.

Example 65

Ethyl 2,7-dimethylimidazo[1,2-a]pyrrolo[3,2-c]pyridine-8-carboxylate (13) and methyl 2,7-dimethylimidazo[1,2-a]pyrrolo[3,2-c]pyridine-8-carboxylate (14)

A mixture of compound 7b (120 mg, 0.50 mmol), dimethyl carbonate (90 mg, 1.00 mmol), potassium carbonate (100 mg) and adogen 464 (25 mg) in dry dimethylformamide (1.5 ml) was stirred, under argon, at 110° C. for 2 h 30 and then concentrated under vacuum. The residue was taken up with water (15 mL), extracted with $CH_2Cl_2$, dried ($Na_2SO_4$), filtered and concentrated under vacuum. The crude residue was purified by chromatography using AcOEt/Hexanes (6/4, v/v) as eluent to give in order of elution: ethyl ester 13 (40 mg, 31%); mp 86-88° C.; IR (KBr) 1704, 1647, 1243 cm$^{-1}$; $^1$H NMR (200 MHz, CDCl$_3$) δ 1.40 (t, 3H, J=7 Hz), 2.46 (s, 3H), 4.10 (s, 3H), 4.37 (q, 2H, J=7 Hz), 6.83 (d, 1H, J=7.5 Hz), 7.22 (s, 1H), 7.74 (s, 1H), 7.84 (d, 1H, J=7.5 Hz); $^{13}$C NMR (100 MHz, CDCl$_3$) δ 14.1, 14.3, 32.6, 60.5, 98.9, 109.4, 109.6, 112.3, 122.9, 126.6, 135.2, 140.5, 141.2, 161.6; MS m/z 257 (M$^+$, 98), 229 (100), 184 (15), 143 (14). Anal. Calcd for $C_{14}H_{15}N_3O_2$: C, 65.35; H, 5.88; N, 16.33. Found: C, 65.48; H, 5.81; N, 16.17. Further elution afforded methyl ester 14 (20 mg, 17%); mp 158-160° C.; IR (KBr) 1701, 1251 cm$^{-1}$; $^1$H NMR (200 MHz, CDCl$_3$) δ 2.45 (s, 3H), 3.90 (s, 3H), 4.08 (s, 3H), 6.79 (d, 1H, J=7.5 Hz), 7.21 (s, 1H), 7.70 (s, 1H), 7.81 (d, 1H, J=7.5 Hz); $^{13}$C NMR (100 MHz, CDCl$_3$) δ 14.1, 32.5, 51.7, 98.9, 105.0, 109.4, 109.6, 112.5, 123.0, 126.3, 135.3, 140.7, 162.0; MS m/z 243 (M$^+$, 100), 212 (21), 184 (19), 143 (13). Anal. Calcd for $C_{13}H_{13}N_3O_2$: C, 64.19; H, 5.39; N, 17.27. Found: C, 64.31; H, 5.51; N, 16.98.

Example 66

2-Methylimidazo[1,2-a]pyrrolo[3,2-c]pyridine-8-carboxylic acid (15)

To a solution of compound 7b (240 mg, 0.99 mmol) in a mixture of THF (1 mL) and ethanol (1 mL) was added a 2N aqueous KOH solution (1 mL, 2 mmol). The solution was stirred at room temperature for 6 h. After cooling at 0° C., the reaction mixture was acidified at pH=1 by addition of concentrated hydrochloric acid. The solid was collected by filtration and dried at 60° C. under vacuum to give acid 15 (210 mg, 99%); mp 325-327° C.; IR (KBr) 3500-3300, 1714, 1669, 1251 cm$^{-1}$; $^1$H NMR (400 MHz, DMSO-d$_6$) δ 2.52 (s, 3H), 7.51 (d, J=7.5 Hz), 7.67 (s, 1H), 8.04 (s, 1H), 8.54 (d, 1H, J=7.5 Hz), 13.18 (brs, 1H); $^{13}$C NMR (100 MHz, DMSO-d$_6$) δ 10.1, 105.2, 106.8, 107.9, 112.2, 124.2, 129.8, 130.2, 135.4, 136.0, 161.5; MS m/z 215 (M$^+$, 44), 197 (60), 171 (100), 170 (92), 143 (14), 117 (15). Anal. Calcd for $C_{11}H_9N_3O_2$: C, 61.39; H, 4.22; N, 19.53. Found: C, 61.71; H, 4.38; N, 19.61.

Example 67

General Procedure for Esterification of Acid 15

Dry hydrogen chloride gas was passed into a solution of acid 15 (110 mg, 0.51 mmol) in appropriate alcohol (20 mL) until saturated. Concentrated sulfuric acid (2 mL) was added and the solution was stirred at reflux for 14 h then concentrated under vacuum. The residue was taken up with cold water (20 mL) and basified (pH=8-9) with 20% aqueous ammonium hydroxide solution. The solution was extracted with $CH_2Cl_2$. The organic layers were washed with saturated aqueous NaCl solution (15 mL), dried ($Na_2SO_4$), filtered and evaporated under vacuum to afforded ester compound 16.

Example 68

Methyl 2-methylimidazo[1,2-a]pyrrolo[3,2-c]pyridine-8-carboxylate (16a)

From methanol (yield: 60%); mp 224-226° C.; IR (KBr) 1698, 1253 cm$^{-1}$; $^1$H NMR (200 MHz, CDCl$_3$) δ 2.45 (s, 3H), 3.92 (s, 3H), 6.85 (d, 1H, J=7.5 Hz), 7.22 (s, 1H), 7.59 (s, 1H), 7.78 (d, 1H, J=7.5 Hz), 10.53 (brs, 1H); $^{13}$C NMR (100 MHz, CDCl$_3$) δ 14.0, 52.0, 100.7, 107.9, 109.7, 114.3, 123.3, 125.9, 132.9, 140.5, 141.3, 162.2; MS m/z 229 (M$^+$, 65), 197 (100), 169 (22), 99 (20). Anal. Calcd for $C_{12}H_{11}N_3O_2$: C, 62.87; H, 4.84; N, 18.33. Found: C, 62.57; H, 4.64; N, 18.59.

Example 69

Butyl 2-methylimidazo[1,2-a]pyrrolo[3,2-c]pyridine-8-carboxylate (16b)

From butanol (yield: 72%); mp 81-83° C.; IR (KBr) 1701, 1257, 1191 cm$^{-1}$; $^1$H NMR (200 MHz, CDCl$_3$) δ 0.94 (t, 3H, J=7.5 Hz), 1.43 (m, 2H), 1.71 (m, 2H), 2.44 (s, 3H), 4.32 (t, 2H, J=6.5 Hz), 6.89 (d, 1H, J=7.5 Hz), 7.21 (s, 1H), 7.57 (s, 1H), 7.77 (d, 1H, J=7.5 Hz), 10.75 (brs, 1H); $^{13}$C NMR (50 MHz, CDCl$_3$) δ 13.6, 13.7, 19.2, 30.7, 65.0, 101.7, 107.7, 110.0, 113.3, 123.1, 126.7, 133.3, 139.2, 140.7, 161.7; MS m/z 271 (M$^+$, 40), 197 (100). Anal. Calcd for $C_{15}H_{17}N_3O_2$: C, 66.40; H, 6.32; N, 15.49. Found: C, 66.22; H, 6.40; N, 15.58.

Example 70

7-Amino-8-bromo-2-methylimidazo[1,2-a]pyridine (18)

To a solution of 2,4-diamino-3-bromopyridine (17) (in Rauckman, B. S, and al. J. Med. Chem. 1980, 23, 384-391) (2.00 g, 10.6 mmol) in ethanol (40 mL) was added chloracetone (3.93 g, 42.5 mmol). The solution was stirred under reflux for 24 h. After cooling to room temperature, the solution was evaporated to dryness. The residue was diluted with water (40 mL) and the resulting solution made basic by the addition of $Na_2CO_3$. The solution was extracted with $CH_2Cl_2$ and the combinated extracts were dried ($Na_2SO_4$), filtered and evaporated under reduced pressure. The crude product was purified by chromatography using $CH_2Cl_2$/EtOAc (4/1, v/v) as eluent to afford compound 18 (yield: 90%); mp 158-160° C.; $^1$H NMR (200 MHz, DMSO-d$_6$) δ 2.19 (s, 3H), 5.78 (brs, 2H), 6.41 (d, 1H, J=7 Hz), 7.36 (s, 1H), 8.07 (d, 1H, J=7 Hz); $^{13}$C NMR (100 MHz, DMSO-d$_6$) δ 14.1, 86.2, 104.6, 109.1, 125.5, 140.8, 143.1, 144.0. Anal.

Example 71

8-Bromo-7-ethoxycarbonylamino-2-methylimidazo[1,2-a]pyridine (19)

A mixture of sodium bicarbonate (0.74 g, 8.81 mmol) and amine 18 (1.00 g, 4.42 mmol) in 50 mL of dry $CH_2Cl_2$ was treated over a period of fifteen minutes with ethyl chloroformate (2.40 g, 22.1 mmol). 4-Dimethylaminopyridine (0.08 g, 0.65 mmol) was added and the reaction mixture was stirred at room temperature for 20 h. Then, water (25 mL) was added and the solution was extracted with $CH_2Cl_2$ (3×25 mL). The extracts were dried ($Na_2SO_4$), filtered and evaporated under vacuum. The residue was purified by chromatography using $CH_2Cl_2$/EtOAc (4/1, v/v) as eluent to afford in order of elution: compound 19 (461 mg, yield: 35%); mp 137-138° C.; $^1$H NMR (200 MHz, $CDCl_3$) δ 1.34 (t, 3H, J=7 Hz), 2.45 (s, 3H), 4.26 (q, 2H, J=7 Hz), 7.24 (brs, 1H), 7.31 (s, 1H), 7.81 (d, 1H, J=7.4 Hz), 7.92 (d, 1H, J=7.4 Hz); $^{13}$C NMR (100 MHz, DMSO-$d_6$) δ 14.1, 14.4, 60.8, 102.5, 109.7, 111.3, 125.1, 133.3, 142.4, 143.0, 153.8. Starting material 18 (0.31 g, 31%).

Example 72

7-ethoxycarbonyl-2-methyl-8-phenylimidazo[1,2-a] pyrrolo[3,2-c]pyridine (20)

To a mixture of $Et_3N$ (10 mL), DMF (75 μL), carbamate 19 (215 mg, 0.72 mmol), $PdCl_2(PPh_3)_2$ (10 mg, 2 mol %) and phenylacetylene (89 mg, 0.87 mmol) stirred 5 min beforehand, CuI (5 mg, 4 mol %) was added and stirring was continued for another 2 min before flushing with Ar. After stirring for 2 days at 60° C., the mixture was concentrated under vacuum. The residue was diluted with water (30 mL) and extracted with $CH_2Cl_2$ (3×30 mL). The organic layers were dried ($Na_2SO_4$), filtered and evaporated under reduced pressure. The residue was purified by chromatography using cyclohexane/EtOAc (4/1, v/v) as eluent to afford compound 20 as an oil (24.8 mg, yield: 11%); $^1$H NMR (400 MHz, $CDCl_3$) δ 1.06 (t, 3H, J=7.1 Hz), 2.48 (s, 3H), 4.25 (q, 2H, J=7.1 Hz), 7.09 (s, 1H), 7.32 (s, 1H), 7.40 (m, 5H), 7.69 (d, 1H, J=7.3 Hz), 7.87 (d, 1H, J=7.3 Hz); $^{13}$C NMR (100 MHz, $CDCl_3$) δ 13.5, 14.2, 63.6, 103.0, 108.1, 109.5, 115.8, 121.5, 127.8, 127.9, 129.0, 132.3, 133.7, 139.7, 140.4, 141.7, 151.3. Anal. Calcd for $C_{19}H_{17}N_3O_2$: C, 71.46; H, 5.37; N, 13.16. Found: C, 72.03; H, 5.42; N, 13.25. Further elution afforded starting material 19 (124 mg, 58%).

Example 73

2,4-diamino-3-iodopyridine (22)

2,4-diaminopyridine 21 (7.89 g, 72.3 mmol) (in Rauckman, B. S, and al. J. Med. Chem. 1980, 23, 384-391) was heated in a mixed solution of acetic acid (90 mL), water (10 mL) and concentrated sulfuric acid (2 mL) at 50° C. for 30 min. After cooling to room temperature, iodine (9.19 g, 36.2 mmol) and periodic acid dihydrate (2.69 g, 11.8 mmol) were added. After stirring for 6 hours at 55° C., the reaction mixture was poured into 10% aqueous $Na_2S_2O_3$ solution to quench any unreacted iodine and then concentrated under vacuum. The residue was diluted with water (250 mL) and basified (pH=7) with solid $NaHCO_3$. A precipitate of 2,4-diamino-3,5-diiodopyridine was isolated (2.46 g, yield: 9%); mp 206° C.; IR (KBr) 3420, 3329, 3263, 3100, 2981, 1601, 1452, 1556; $^1$H NMR (200 MHz, DMSO-$d_6$) δ 5.59 (s, 2H), 5.84 (s, 2H); 7.78 (s, 1H); $^{13}$C NMR (50 MHz, DMSO-$d_6$) δ 62.9, 65.7, 152.6, 153.5, 159.3. Anal. Calcd for $C_5H_5I_2N_3$: C, 16.64; H, 1.40; N, 11.64. Found: C, 16.78; H, 1.22; N, 11.49. The filtrate was extracted with EtOAc (3×200 mL) to give 2,4-diamino-3-iodopyridine 22 (15.33 g, yield: 90%); mp 140° C.; IR (KBr) 3451, 3398, 3298, 3175, 1618, 1587, 1534, 1436 cm$^{-1}$; $^1$H NMR (200 MHz, DMSO-$d_6$) δ 5.55 (s, 2H), 5.79 (s, 2H), 5.94 (d, 1H, J=5.5 Hz), 7.40 (d, 1H, J=5.5 Hz); $^{13}$C NMR (50 MHz, DMSO-$d_6$) δ 64.1, 100.4, 146.9, 154.9, 159.18. Anal. Calcd for $C_5H_6IN_3$: C, 25.55; H, 2.57; N, 17.88. Found: C, 25.67; H, 2.83; N, 17.91.

Example 74

7-Amino-8-iodo-2-methylimidazo[1,2-a]pyridine (23)

To a solution of 2,4-diamino-3-iodopyridine 22 (4.36 g, 18.6 mmol) in ethanol (100 mL) was added chloracetone (7.15 g, 77.3 mmol). The solution was stirred at 65° C. for 6 h. After cooling to room temperature, the solution was evaporated to dryness. The residue was diluted with water (75 mL) and the resulting solution made basic (pH=12-13) by the addition of a ammonium hydroxide solution. The solution was extracted with $CH_2Cl_2$ and the combinated extracts were dried ($Na_2SO_4$), filtered and evaporated under reduced pressure. The crude product was purified by chromatography using $CH_2Cl_2$/EtOAc (4/1, v/v) as eluent to afford compound 23 (3.30 g, yield: 65%); mp 185° C.; IR (KBr) 3454, 3431, 3355, 3093, 3026, 1646, 1499, 1463; $^1$H NMR (400 MHz, DMSO-$d_6$) δ 2.19 (s, 3H), 5.68 (brs, 2H), 6.38 (d, 1H, J=7.1 Hz), 7.42 (s, 1H), 8.03 (d, 1H, J=7.1 Hz); $^{13}$C NMR (100 MHz, DMSO-$d_6$) δ 14.1, 60.9, 103.8, 109.3, 126.0, 140.4, 145.6, 146.6. Anal. Calcd for $C_8H_8IN_3$: C, 35.19; H, 2.95; N, 15.39. Found: C, 35.25; H, 2.92; N, 15.60.

Example 75

8-iodo-7-ethoxycarbonylamino-2-methylimidazo[1,2-a]pyridine (24)

A mixture of sodium carbonate (0.57 g, 5.38 mmol) and amine 23 (1.47 g, 5.38 mmol) in 50 mL of dry $CH_2Cl_2$ was treated, under argon, over a period of 15 min with ethyl chloroformate (2.34 g, 22.6 mmol). The reaction mixture was stirred at room temperature for 24 h. Then, water (50 mL) was added and organic layer was recovered, the aqueous layer was extracted with additional $CH_2Cl_2$ (3×50 mL). The organic extracts were dried ($Na_2SO_4$), filtered and evaporated under vacuum. The residue was purified by chromatography using $CH_2Cl_2$/EtOAc (4/1, v/v) as eluent to afford in order of elution: Compound 24 (820 mg, yield: 44%); mp 148° C.; IR (KBr) 3380, 3124, 3049, 2988, 1738, 1642, 1541; $^1$H NMR (400 MHz, DMSO-$d_6$) δ 1.25 (t, 3H, J=7.1 Hz), 2.31 (s, 3H), 4.13 (q, 2H, J=7.1 Hz), 6.93 (d, 1H, J=7.1 Hz), 7.78 (s, 1H), 8.35 (d, 1H, J=7.1 Hz), 8.93 (s, 1H); $^{13}$C NMR (100 MHz, DMSO-$d_6$) δ 14.1, 14.5, 60.7, 81.8, 110.1, 111.5, 125.7, 137.2, 142.7, 144.5, 153.9. Anal. Calcd for $C_{11}H_{12}IN_3O_2$: C, 38.28; H, 3.50; N, 12.18. Found: C, 38.04; H, 3.55; N, 12.08. Starting material 23 (0.66 g, 45%).

Example 76

General Procedure for the Palladium-Catalyzed Cross-Coupling Reaction of Compound 24 with Terminal Alkynes A mixture of carbamate 24 (1 mmol), an alkyne (1.2 mmol), $PdCl_2(PPh_3)_2$ (2 mol %), CuI (20 mol %), $Et_3N$ (3 mmol) and DMF (20 mL) was flushing with argon and stirring for 2 days at room temperature. After removal of the solvent, the residue was diluted with $H_2O$ (25 mL) and extracted with $CH_2Cl_2$ (3×25 mL). The $CH_2Cl_2$ extracts were dried ($Na_2SO_4$), filtered and evaporated. The residue was purified by chromatography using cyclohexane/EtOAc (4/1, v/v) as eluent to afford compound 25.

Example 77

Ethyl [8-[2-(4-methoxyphenyl)ethynyl]-2-methylimidazo[1,2-a]pyridine-7-yl]carbamate (25a)

From 1-ethynyl-4-methoxybenzene (yield: 25%); mp 141° C.; IR (KBr) 3383, 3053, 2917, 2201, 1727, 1629, 1602, 1559, 1509 cm$^{-1}$; $^1$H NMR (400 MHz, DMSO-d$_6$) δ 1.25 (t, 3H, J=7.1 Hz), 2.32 (s, 3H), 3.81 (s, 3H), 4.17 (q, 2H, J=7.1 Hz), 7.03 (d, 2H, J=8.8 Hz), 7.24 (d, 1H, J=7.6 Hz), 7.56 (d, 2H, J=8.8 Hz), 7.63 (s, 1H), 8.39 (d, 1H, J=7.2 Hz), 9.17 (s, 1H); $^{13}$C NMR (100 MHz, DMSO-d$_6$) δ 14.2, 14.5, 55.3, 60.9, 80.8, 99.5, 100.7, 107.8, 110.2, 114.4, 114.5, 126.0, 133.1, 137.0, 142.6, 143.7, 153.6, 159.7. Anal. Calcd for C$_{20}$H$_{19}$N$_3$O$_3$: C, 68.75; H, 5.48; N, 12.03. Found: C, 69.10; H, 5.57; N, 12.06.

Example 78

Ethyl [8-[2-(4-fluorophenyl)ethynyl]-2-methylimidazo[1,2-a]pyridine-7-yl]carbamate (25b)

From 1-ethynyl-4-fluorobenzene (yield: 70%); mp 175° C.; IR (KBr) 3406, 3054, 2981, 2193, 1740, 1633, 1599, 1564, 1234 cm$^{-1}$; $^1$H NMR (400 MHz, DMSO-d$_6$) δ 1.25 (t, 3H, J=7.2 Hz), 2.32 (s, 3H), 4.17 (q, 2H, J=7.1 Hz), 7.30 (m, 3H), 7.63 (s, 1H), 7.70 (m, 2H), 8.41 (d, 1H, J=7.4 Hz), 9.31 (s; 1H); $^{13}$C NMR (100 MHz, DMSO-d$_6$) δ 14.2, 14.5, 61.0, 81.9, 98.2, 100.1, 107.8, 110.3, 116.0 (d, $^2J_{CF}$=22.0 Hz), 119.1, 126.4, 133.9 (d, $^3J_{CF}$=8.5 Hz), 137.6, 142.7, 143.7, 153.7, 162.2 (d, $^1J_{CF}$=246.3 Hz). Anal. Calcd for C$_{19}$H$_{16}$FN$_3$O$_2$: C, 67.65; H, 4.78; N, 12.46. Found: C, 67.62; H, 4.51; N, 12.59.

Example 79

Ethyl [8-(hex-1-ynyl)-2-methylimidazo[1,2-a]pyridine-7-yl]carbamate (25c)

From 1-hexyne (yield: 61%); as an viscous oil; IR (KBr) 3379, 2958, 2227, 1731, 1632, 1567 cm$^{-1}$; $^1$H NMR (200 MHz, CDCl$_3$) δ 0.93 (t, 3H, J=7.1 Hz), 1.29 (t, 3H, J=7.1 Hz), 1.50 (m, 2H), 1.61 (m, 2H), 2.39 (s, 3H), 2.59 (t, 2H, J=7.0 Hz), 4.21 (q, 2H, J=7.1 Hz), 7.17 (s, 1H), 7.51 (brs, 1H), 7.76 (d, 1H, J=7.5 Hz), 7.86 (d, 1H, J=7.5 Hz); $^{13}$C NMR (50 MHz, CDCl$_3$) δ 13.5, 14.2, 14.3, 19.8, 22.0, 30.5, 61.5, 71.2, 96.9, 104.0, 104.2, 109.0, 124.5, 137.7, 143.6, 144.6, 152.9. Anal. Calcd for C$_{17}$H$_{21}$N$_3$O$_2$: C, 68.21; H, 7.07; N, 14.04. Found: C, 68.44; H, 7.09; N, 13.97.

Example 80

Ethyl 8-(4-methoxyphenyl)-2-methylimidazo[1,2-a]pyrrolo[3,2-c]pyridine-7-carboxylate (26a)

A solution of 25a (150 mg, 0.43 mmol) and Cu(OAc)$_2$ (15.6 mg, 85.9 μmol) in anhydrous 1,2-dichloroethane (10 mL) was heated, under argon, at 65° C. for 4 days. After removal of the solvent, the residue was diluted with H$_2$O (10 mL) and extracted with CH$_2$Cl$_2$ (3×10 mL). The CH$_2$Cl$_2$ extracts were dried (Na$_2$SO$_4$), filtered and evaporated. The residue was purified by chromatography using cyclohexane/EtOAc (4/1, v/v) as eluent to afford in order of elution: compound 26a (25 mg, yield: 17%); mp 158-159° C.; IR (KBr) 3112, 2959, 1736, 1634, 1611, 1499, 1304 cm$^{-1}$; $^1$H NMR (400 MHz, CDCl$_3$) δ 1.13 (t, 3H, J=7.5 Hz), 2.47 (s, 3H), 3.85 (s, 3H), 4.27 (q, 2H, J=7.5 Hz), 6.93 (d, 2H, J=8.8 Hz), 7.02 (s, 1H), 7.31 (s, 1H), 7.34 (d, 2H, J=8.8 Hz), 7.66 (d, 1H, J=7.5 Hz), 7.86 (d, 1H, J=7.5 Hz); $^{13}$C NMR (100 MHz, CDCl$_3$) δ 13.9, 14.4, 55:5, 63.7, 103.2, 107.8, 109.5, 113.4, 116.1, 121.4, 126.3, 130.4, 132.1, 139.7, 140.7, 141.9, 151.5, 159.6. Anal. Calcd for C$_{20}$H$_{19}$N$_3$O$_3$: C, 68.75; H, 5.48; N, 12.03. Found: C, 68.59; H, 5.77; N, 12.23.
Starting material 25a (76 mg, yield: 51%)

Example 81

Ethyl 8-(4-fluorophenyl)-2-methylimidazo[1,2-a]pyrrolo[3,2-c]pyridine-7-carboxylate (26b)

A solution of 25b (125 mg, 0.37 mmol) and Cu(OAc)$_2$ (13.5 mg, 74.3 μmol) in anhydrous 1,2-dichloroethane (10 mL) was heated, under argon, at 65° C. for 4 days. After removal of the solvent, the residue was diluted with H$_2$O (10 mL) and extracted with CH$_2$Cl$_2$ (3×10 mL). The organic extracts were dried (Na$_2$SO$_4$), filtered and evaporated. The residue was purified by chromatography using cyclohexane/EtOAc (4/1, v/v) as eluent to afford in order of elution: compound 26b (55 mg, yield: 44%); mp 175° C.; IR (KBr) 3018, 2913, 1746, 1645, 1497, 1140 cm$^{-1}$; $^1$H NMR (400 MHz, DMSO-d$_6$) δ 1.08 (t, 3H, J=7.2 Hz), 2.34 (s, 3H), 4.27 (q, 2H, J=7.2 Hz), 6.98 (s, 1H), 7.27 (m, 2H), 7.55 (m, 2H), 7.60 (d, 1H, J=7.2 Hz), 7.67 (s, 1H), 8.32 (d, 1H, J=7.2 Hz); $^{13}$C NMR (100 MHz, DMSO-d$_6$) δ 13.4, 14.2, 63.7, 102.0, 107.5, 110.0, 114.7 (d, $^2J_{CF}$=20.1 Hz), 116.2, 122.9, 129.5, 130.9 (d, $^3J_{CF}$=8.1 Hz), 131.4, 137.8, 139.3, 140.8, 150.5, 161.8 (d, $^1J_{CF}$=243.1 Hz). Anal. Calcd for C$_{19}$H$_{16}$FN$_3$O$_2$: C, 67.65; H, 4.78; N, 12.46. Found: C, 67.52; H, 4.87; N, 12.25.
Starting material 25b (19 mg, yield: 15%)

Example 82

General Procedure for the Cyclisation Reaction of 25a-c Compounds with Tetrabutylammonium Fluoride (TBAF)

A mixture of compound 25 (0.4 mmol), a 1M solution of TBAF in THF (1.2 mL, 1.2 mmol) and THF (5 mL) was refluxed for 20 hours. After removal of the THF under reduced pressure, the residue was diluted with H$_2$O (10 mL), basified with Na$_2$CO$_3$ (pH=12) and extracted with CH$_2$Cl$_2$ (3×10 mL). The organic layers were dried (Na$_2$SO$_4$), filtered and evaporated. The residue was purified by chromatography using CH$_2$Cl$_2$/EtOAc (4/1, v/v) as eluent to afford compound 27.

Example 83

8-(4-methoxyphenyl)-2-methylimidazo[1,2-a]pyrrolo[3,2-c]pyridine (27a)

From 25a (yield: 35%); mp 168° C.; IR (KBr) 3422, 3053, 2917, 2827, 1637, 1521, 1490, 1307, 1027 cm$^{-1}$; $^1$H NMR (400 MHz, DMSO-d$_6$) δ 2.30 (s, 3H), 3.80 (s, 3H), 6.93 (d, 1H, J=7.6 Hz), 7.01 (d, 1H, J=2.0 Hz), 7.03 (m, 2H), 7.49 (s, 1H), 7.77 (m, 2H), 8.02 (d, 1H, J=7.2 Hz), 11.83 (s, 1H); $^{13}$C NMR (100 MHz, DMSO-d$_6$) δ 14.2, 55.2, 96.8, 100.5, 109.2, 114.2, 114.4, 120.3, 124.6, 126.0, 131.0, 135.8, 139.0, 140.8,

Example 84

8-(4-fluorophenyl)-2-methylimidazo[1,2-a]pyrrolo[3,2-c]pyridine (27b)

From 25b (yield: 43%); 280° C. (dec.); IR (KBr) 3461, 3119, 2917, 1645, 1521, 1489, 1229 cm$^{-1}$; $^1$H NMR (400 MHz, DMSO-d$_6$) δ 2.31 (s, 3H), 6.96 (d, 1H, J=7.2 Hz), 7.12 (d, 1H, J=1.6 Hz), 7.30 (m, 2H), 7.51 (s, 1H), 7.88 (m, 2H), 8.06 (d, 1H, J=7.2 Hz), 11.98 (s, 1H); $^{13}$C NMR (100 MHz, DMSO-d$_6$) δ 14.2, 98.1, 100.6, 109.4, 114.1, 115.9 (d, $^2J_{CF}$=22.0 Hz), 120.9, 126.6 (d, $^3J_{CF}$=7.9 Hz), 128.6, 131.5, 134.8, 139.0, 140.7, 161.3 (d, $^1J_{CF}$=242.8 Hz). Anal. Calcd for C$_{16}$H$_{12}$FN$_3$: C, 72.44; H, 4.56; N, 15.84. Found: C, 72.78; H, 4.12; N, 16.15.

Example 85

8-butyl-2-methylimidazo[1,2-a]pyrrolo[3,2-c]pyridine (27c)

From 25c (yield: 55%); mp 162° C.; IR (KBr) 3061, 2924, 1637, 1528 cm$^{-1}$; $^1$H NMR (400 MHz, CDCl$_3$) δ 0.82 (t, 3H, J=7.6 Hz), 1.28 (m, 2H), 1.60 (m, 2H), 2.43 (s, 3H), 2.69 (t, 2H, J=7.6 Hz), 6.56 (s, 1H), 6.82 (d, 1H, J=7.1 Hz), 7.20 (s, 1H), 7.62 (d, 1H, J=7.1 Hz), 10.37 (s, 1H); $^{13}$C NMR (100 MHz, CDCl$_3$) δ 13.8, 14.2, 22.3, 27.8, 31.5, 98.8, 101.2, 108.9, 114.1, 118.8, 130.4, 139.1, 139.8, 142.0. Anal. Calcd for C$_{14}$H$_{17}$N$_3$: C, 73.98; H, 7.54; N, 18.49. Found: C, 74.05; H, 7.51; N, 18.29.

Example 86

2,2,2-trifluoro-N-(8-iodo-2-methylimidazo[1,2-a]pyridine-7-yl)acetamide (28)

A mixture of amine 23 (300 mg, 1.10 mmol) and dry CH$_2$Cl$_2$ (20 mL) was flushed with argon. Then trifluoroacetic anhydrate (347 mg; 1.65 mmol) was added with a syringe. The reaction mixture was stirred at room temperature for 15 h. After solvent removal under reduced pressure, water (10 mL) was added and the mixture was basified carefully between pH=6 and pH=7 with aqueous buffer solution containing H$_2$PO$_4^-$/HPO$_4^{2-}$ ions. The resulting solution was extracted with EtOAc (4×25 mL). The organic extracts were dried (Na$_2$SO$_4$), filtered and evaporated under vacuum. The residue was purified by silica gel column chromatography using EtOAc/MeOH (99/1, v/v) as eluent to afford compound 28 (193 mg, yield: 48%); mp 168° C.; IR (KBr) 3115, 2955, 2831, 1716, 1622, 1558, 1541, 1456; $^1$H NMR (400 MHz, DMSO-d$_6$) δ 2.35 (s, 3H), 6.87 (d, 1H, J=6.8 Hz), 7.89 (s, 1H), 8.47 (d, 1H, J=6.8 Hz), 11.38 (brs, 1H); $^{13}$C NMR (100 MHz, DMSO-d$_6$) δ 14.1, 86.6, 111.4, 112.3, 116.1 (q, $^1J_{CF}$=286.6 Hz), 126.3, 134.6, 143.4, 144.2, 155.2 (q, $^2J_{CF}$=38.1 Hz). Anal. Calcd for C$_{10}$H$_7$F$_3$IN$_3$O: C, 32.54; H, 1.91; N, 11.39. Found: C, 32.55; H, 1.87; N, 11.46.

Example 87

2-methyl-8-phenylimidazo[1,2-a]pyrrolo[3,2-c]pyridine (29)

A mixture of 28 (200 mg, 0.54 mmol), phenylacetylene (83 mg, 0.81 mmol), [Cu(Phen)(PPh$_3$)$_2$]NO$_3$ (45 mg, 54.0 μmol), K$_3$PO$_4$ (230 mg, 1.08 mmol) and anhydrous DMF (5 mL) was flushed with argon and stirred for 2 days at 115° C. After removal of the solvent, the residue was diluted with H$_2$O (25 mL) and extracted with CH$_2$Cl$_2$ (5×20 mL). The CH$_2$Cl$_2$ extracts were dried (Na$_2$SO$_4$), filtered and evaporated. The residue was purified by chromatography using CH$_2$Cl$_2$/EtOAc (4/1, v/v) as eluent to afford compound 29 (75 mg, yield: 56%); mp 222° C.; IR (KBr) 3026, 3057, 2944, 2824, 1641, 1604, 1535 cm$^{-1}$; $^1$H NMR (400 MHz, DMSO-d$_6$) δ 2.3 (s, 3H), 6.96 (d, 1H, J=7.2 Hz), 7.15 (s, 1H), 7.29 (t, 1H, J=7.4 Hz), 7.46 (t, 2H, J=7.8 Hz), 7.50 (s, 1H), 7.85 (d, 2H, J=8.4 Hz), 8.06 (d, 1H, J=7.2 Hz), 11.98 (s, 1H); $^{13}$C NMR (100 MHz, DMSO-d$_6$) δ 14.2, 98.1, 100.6, 109.3, 114.2, 120.9, 124.5, 127.1, 128.9, 131.4, 131.9, 135.7, 139.1, 140.7. Anal. Calcd for C$_{16}$H$_{13}$N$_3$: C, 77.71; H, 5.30; N, 16.99. Found: C, 77.69; H, 5.41; N, 16.94.

Example 88

N-allyl-8-iodo-2-methylimidazo[1,2-a]pyridin-7-amine (30)

To a solution of 23 (250 mg, 0.92 mmol) in anhydrous THF (20 mL), NaH (60% in mineral oil, 44 mg, 1.098 mmol), allyl bromide (133 mg, 1.10 mmol) and tetrabutylammonium bromide (354 mg, 1.10 mmol) were added under argon atmosphere. The mixture was stirred for 15 h at room temperature. After removal of the solvent, the residue was diluted with H$_2$O (20 mL) and extracted with CH$_2$Cl$_2$ (3×20 mL). The CH$_2$Cl$_2$ extracts were dried (Na$_2$SO$_4$), filtered and evaporated. The residue was purified by chromatography using CH$_2$Cl$_2$/EtOAc (4/1, v/v) as eluent to afford compound 30 (156 mg, yield: 54%); as an oil; $^1$H NMR (400 MHz, CDCl$_3$) δ 2.40 (s, 3H), 3.92 (m, 2H), 4.70 (m, 1H), 5.22 (m, 2H), 5.93 (m, 1H), 6.25 (d, 1H, J=7.3 Hz), 7.21 (s, 1H), 7.75 (d, 1H, J=7.3 Hz); $^{13}$C NMR (100 MHz, CDCl$_3$) δ 14.5, 46.6, 64.3, 100.7, 109.1, 116.8, 125.7, 134.5, 142.7, 145.8, 146.3. Anal. Calcd for C$_{11}$H$_{12}$IN$_3$: C, 42.19; H, 3.86; N, 13.42. Found: C, 42.39; H, 3.95; N: 1328.

Example 89

2,9-dimethylimidazo[1,2-a]pyrrolo[3,2-c]pyridine (31)

A mixture of 30 (117 mg, 0.37 mmol), anhydrous DMF (5 mL), Et$_3$N (130 μL, 0.94 mmol), tetrabutylammonium chloride (104 mg, 0.37 mmol), Pd(OAc)$_2$ (9 mg, 40.1 μmol) was stirred for 3 days at room temperature. After removal of the solvent, the residue was diluted with H$_2$O (10 mL), basified with Na$_2$CO$_3$ to pH=10-12 and extracted with CH$_2$Cl$_2$ (3×20 mL). The CH$_2$Cl$_2$ extracts were dried (Na$_2$SO$_4$), filtered and evaporated. The residue was purified by chromatography using CH$_2$Cl$_2$/EtOAc (4/1, v/v) as eluent to afford compound 31 (26 mg, yield: 38%); mp 211° C.; IR (KBr) 3099, 3068, 3006, 2913, 2858, 1633, 1517 cm$^{-1}$; $^1$H NMR (400 MHz, CDCl$_3$) δ 2.45 (s, 3H), 2.61 (s, 3H), 6.78 (d, 1H, J=7.2 Hz), 6.90 (s, 1H), 7.22 (s, 1H), 7.66 (d, 1H, J=7.2 Hz), 9.55 (brs, 1H); $^{13}$C NMR (100 MHz, CDCl$_3$) δ 11.9, 14.3, 101.5, 109.0, 113.3, 113.7, 119.8, 120.6, 131.1, 140.0, 142.6. Anal. Calcd for C$_{11}$H$_{11}$N$_3$: C, 71.33; H, 5.99; N, 22.69. Found: C, 70.94; H, 5.89; N, 23.01.

Part B: Methodology for and Results of the Determination of Antiviral and Cytostatic Activity Example 90

Determination and Investigation of the Anti-Viral Activity

Cells and Viruses

Madin-Darbey Bovine Kidney (MDBK) cells were maintained in Dulbecco's modified Eagle medium (DMEM) supplemented with BVDV-free 5% fetal calf serum (DMEME-FCS) at 37° C. in a humidified, 5% $CO_2$ atmosphere. BVDV-1 (strain PE515) was used to assess the antiviral activity in MDBK cells.

Determination of Cytostatic Effect on MDBK Cells

The effect of the drugs on exponentially growing MDBK cells was assessed as follows. Cells were seeded at a density of 5000 cell/well in 96 well plates in MEM medium (Gibco) supplemented with 10% fetal calf serum, 2 mM L-glutamine (Life Technologies) and bicarbonate (Life Technologies). Cells, were cultured for 24 hr after which serial dilutions of the test compounds were added. Cultures were then again further incubated for 3 days after which the effect on cell growth was quantified by means of the MTS method (Promega). The concentration that results in 50% inhibition of cell growth is defined as the 50% cytostatic concentration ($CC_{50}$)

Anti-BVDV Assay

Ninety-six-well cell culture plates were seeded with MDBK cells in DMEM-FCS so that cells reached 24 hr later confluency. Then medium was removed and serial 5-fold dilutions of the test compounds were added in a total volume of 100 μl, after which the virus inoculum (100 μl) was added to each well. The virus inoculum used resulted in a greater than 90% destruction of the cell monolayer after 5 days incubation at 37° C. Uninfected cells and cells receiving virus without compound were included in each assay plate. After 5 days, medium was removed and 90 μl of DMEM-FCS and 10 μl of MTS/PMS solution (Promega) was added to each well. Following a 2 hr incubation period at 37° C. the optical density of the wells was read at 498 nm in a microplate reader. The 50% effective concentration ($EC_{50}$) value was defined as the concentration of compound that protects 50% of the cell monolayer from virus-induced cytopathic effect.

Example 91

Anti-BVDV Activity

The results of the testing of the compounds of the invention for their anti-BVDV activity with the assay, described above are provided in Table 1 hereunder.

TABLE 1

Anti-BVDV activity of compounds of the invention

| Compound Code | EC50 (μg/mL) | CC50 (μg/mL) | SI |
|---|---|---|---|
| 7i | 1.5 | >50 | >33 |
| 7b | 0.8 | 65 | ±81 |
| 9 | 4 | 41 | ±10 |
| 7h | 3 | 22 | ±7 |
| 7e | 1.5 | >50 | ±33 |
| 7f | 0.6 | 22 | ±36 |
| 15 | 0.5 | >100 | >200 |
| 9 | 3 | 85 | ±28 |

TABLE 1-continued

Anti-BVDV activity of compounds of the invention

| Compound Code | EC50 (μg/mL) | CC50 (μg/mL) | SI |
|---|---|---|---|
| 11 | 9 | 87 | ±10 |
| 26b | 1.25 | 7.9 | ±6 |
| 27b | 1.27 | 47.5 | ±37 |

SI: Selectivity index (ratio of $CC_{50}$ to $EC_{50}$)

The invention claimed is:

1. A compound according to general formula (I), or a pharmaceutically acceptable salt, solvate, tautomer, or enantiomer thereof,

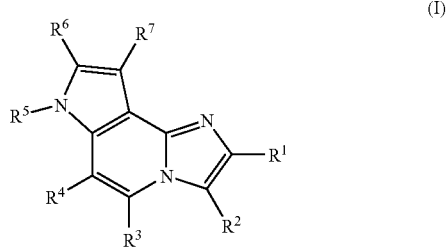

(I)

wherein:
each of $R^1$, $R^2$, $R^3$, $R^4$, $R^6$ and $R^7$ are independently selected from the group consisting of hydrogen, —OH, —SH, —NH$_2$, —NO$_2$, halogen, tri-$C_{1-16}$-alkylsilyl, and a $C_{1-16}$ hydrocarbyl group which optionally includes one or more heteroatoms at any position of said hydrocarbyl group (in the main or side chains), wherein said heteroatoms are selected from the group consisting of O, S, and N and wherein said hydrocarbyl group is unsubstituted or substituted with one or more $Z^1$, and wherein $R^2$ is not a substituted or unsubstituted amine, $R^5$ is hydrogen, or a $C_{1-16}$ hydrocarbyl group which optionally includes one or more heteroatoms at any position of the hydrocarbyl group (in the main or side chains), wherein heteroatoms are selected from the group consisting of O, S, and N and wherein said hydrocarbyl group is unsubstituted or substituted with one or more $Z^1$, $Z^1$ is selected from the group consisting of —OH, —SH, —NH$_2$, halogen, —OCF$_3$, —NO$_2$, and a $C_{1-16}$ hydrocarbyl group which optionally includes one or more heteroatoms at any position of the hydrocarbyl group (in the main or side chains), wherein said heteroatoms are selected from the group consisting of O, S, and N, and which compound is not selected from the following compounds:
imidazo[1,2-a]pyrrolo[3,2-c]pyridine,
ethyl 2-bromoimidazo[1,2-a]pyrrolo[3,2-c]pyridine-8-carboxylate, and
ethyl imidazo[1,2-a]pyrrolo[3,2-c]pyridine-8-carboxylate.

2. The compound according to claim 1, wherein:
said $C_{1-16}$ hydrocarbyl groups are selected from the group consisting of $C_{1-16}$ alkyl (including haloalkyl), $C_{2-16}$ alkenyl, $C_{2-16}$ alkynyl, $C_{1-16}$ alkoxy, $C_{1-16}$ alkylthio, $C_{3-16}$ cycloalkyl, $C_{4-16}$ cycloalkenyl, $C_{4-16}$ cycloalkynyl, aryl, aryloxy, arylthio, arylalkyl, heterocycle, oxyheterocycle, and thioheterocycle,
each $Z^2$ and $Z^3$ is hydrogen or $C_{1-16}$ alkyl.

3. The compound according to claim 1, wherein $R^3$ and $R^4$ are hydrogen.

4. The compound according to claim 3, wherein
$R^1$ is selected from the group consisting of hydrogen, halogen, $C_{1-16}$ alkyl (including haloalkyl), $C_{1-16}$ alkoxy, aryl, aryloxy, and arylalkyl, wherein each of said alkyl, alkoxy, aryl, aryloxy and arylalkyl is substituted with 1 or more
$R^2$ is hydrogen, halogen or —$NO_2$,
$R^5$ is selected from the group consisting of hydrogen, $C_{1-16}$ alkyl (including haloalkyl), and —$C(=O)Z^4$,
$R^6$ is selected from the group consisting of hydrogen, aryl, $C_{1-16}$ alkyl (including haloalkyl), and —$C(=O)Z^4$,
$R^7$ is hydrogen or $C_{1-16}$ alkyl (including haloalkyl),
$Z^1$ is selected from the group consisting of $C_{1-16}$ alkyl (including haloalkyl), $C_{1-16}$ alkoxy, halogen, —OH, —$NZ^2Z^3$, aryl, aryloxy and arylalkyl,
each $Z^2$ and $Z^3$ is independently selected from hydrogen, $C_{1-16}$ alkyl and aryl,
$Z^4$ is selected from hydrogen, OH, $C_{1-16}$ alkyl, $C_{1-16}$ alkoxy, $NZ^2Z^3$, aryl, and aryloxy.

5. A pharmaceutical composition comprising a compound according to formula (I), or a pharmaceutically acceptable salt, solvate, tautomer, or enantiomer thereof,

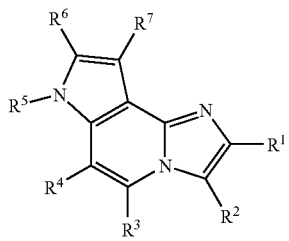

(I)

wherein:
each of $R^1$, $R^2$, $R^3$, $R^4$, $R^6$ and $R^7$ are independently selected from hydrogen, —OH, —SH, —$NH_2$, —$NO_2$, halogen, tri-$C_{1-16}$-alkylsilyl, and a $C_{1-16}$ hydrocarbyl group which optionally includes one or more heteroatoms at any position of the hydrocarbyl group (in the main or side chains), said heteroatoms being selected from the group consisting of O, S, and N and wherein said hydrocarbyl group is unsubstituted or substituted with one or more $Z^1$, and wherein $R^2$ is not a substituted or unsubstituted amine,
$R^5$ is hydrogen or a $C_{1-16}$ hydrocarbyl group which optionally includes one or more heteroatoms at any position of the hydrocarbyl group (in the main or side chains), said heteroatoms being selected from the group consisting of O, S, and N and wherein said hydrocarbyl group is unsubstituted or substituted with one or more $Z^1$,
$Z^1$ is selected from the group consisting of —OH, —SH, —$NH_2$, halogen, —$OCF_3$, —$NO_2$, and a $C_{1-16}$ hydrocarbyl group which optionally includes one or more heteroatoms at any position of the hydrocarbyl group (in the main or side chains), said heteroatoms being selected from the group consisting of O, S, and N,
and which compound is not selected from the following compounds:
ethyl 2-bromoimidazo[1,2-a]pyrrolo[3,2-c]pyridine-8-carboxylate, and
ethyl imidazo[1,2-a]pyrrolo[3,2-c]pyridine-8-carboxylate,
as an active ingredient in admixture with a pharmaceutically acceptable carrier.

* * * * *